US007196169B2

(12) United States Patent
Van Eyk et al.

(10) Patent No.: US 7,196,169 B2
(45) Date of Patent: Mar. 27, 2007

(54) ISOLATED POST-TRANSLATIONALLY MODIFIED MAMMALIAN PROTEINS FOR MONITORING AND DIAGNOSING MUSCLE DAMAGE

(75) Inventors: Jennifer E. Van Eyk, Kingston (CA); Jeremy A. C. Simpson, Kingston (CA); Ninetta Buscemi, Edmonton (CA); Michelle K. Quick, Kingston (CA)

(73) Assignee: Queen's University at Kingston, Kingston (CA)

( * ) Notice: Subject to any disclaimer, the term of this patent is extended or adjusted under 35 U.S.C. 154(b) by 628 days.

(21) Appl. No.: 10/270,838

(22) Filed: Oct. 11, 2002

(65) Prior Publication Data

US 2004/0072255 A1   Apr. 15, 2004

(51) Int. Cl.
*C07K 14/00* (2006.01)
(52) U.S. Cl. ..................................... 530/350
(58) Field of Classification Search ................. 530/350
See application file for complete search history.

(56) References Cited

U.S. PATENT DOCUMENTS 5,834,220 A   11/1998   Wicks et al. ............... 435/7.92
6,248,549 B1   6/2001   Van Eyk et al. ............... 435/15

FOREIGN PATENT DOCUMENTS

| CA | 2243372 | 7/1998 |
|---|---|---|
| WO | WO 94/27156 | 11/1994 |
| WO | WO 96/10078 | 4/1996 |
| WO | WO 96/33415 | 10/1996 |

OTHER PUBLICATIONS

Ardelt et al. 1998; Microanalysis and distribution of cardiac troponin I phopho species in heart areas. Biol. Chem. 379:341-347.*
Jaquet et al. 1995; Pattern formation on cardiac troponin by consecutive phosphorylation and dephosphorylation. Eur. J. Biochem. 231: 486-490.*
Swiderek et al. 1990; Sites phosphorylated in bovine cardiac troponin T and I. Eur. J. Biochem. 190:575-582.*
Buscemi et al., "p21-Activated Kinase Increases the Calcium Sensitivity of Rat Triton-Skinned Cardiac Muscle Fiber Bundles via a Mechanism Potentially Involving Novel Phosphorylation of Troponin I", Circ. Res. 2002 91:509-516.
Härtner and Pette, "Fast and slow isoforms of troponin I and troponin C. Distribution in normal rabbit muscles and effects of chronic stimulation", Eur. J. Biochem. 1990 188:261-267.
U.S. Appl. No. 09/419,901, filed Oct. 18, 1999, Van Eyk et al.
Bartel, S., et al., Protein Phosphorylation in Isolated Trabeculae from Nonfailing and Failing Human Hearts. (Abstract) *Mol. Cell Biochem.*, 157: 171-179 (1996).
Bodor, G. S., et al., Troponin I Phosphorylation in the Normal and Failing Adult Human Heart. *Circulation*, 96: 1495-1500 (1997).
Collinson, P.O., et al., Measurement of Cardiac Troponins. *Ann. Clin. Biochem.* 38(Pt 5): 423-449 (2001).

Jideama, N.M., et al., Phosphorylation Specificities of Protein Kinase C Isozymes for Bovine Cardiac Troponin I and Troponin T and Sites Within there Proteins and Regulation of Myofilament Properties. *J. Biol. Chem.*, 271: 23277-23283 (1996).
Kaumann, A., et al., Activation of β2-Adrenergic Receptors Hastens Relaxation and Mediates Phosphorylation of Phospholamban, Troponin I, and C-Protein in Ventricular Myocardium from Patients with Terminal Heart Failure. *Circulation* 99: 65-72 (1999).
Matejovicova, M., et al., Phosphorylation by Protein Kinases A and C of Myofibrillar Proteins in Rabbit Stunned and Non-Stunned Myocardium. *J. Mol. Cell Cardiol.* 29: 3189-3202 (1997).
McConnell, B. K., et al., Troponin I Phosphorylation and Myofilament Calcium Sensitivity During Decompensated Cardiac Hypertrophy. *Amer. J. Physiol.* 274 (Heart Circ. Physiol. 43): H385-H396 (1998).
Takahashi, M., et al., Use of Enzyme Immunoassay for Measurement of Skeletal Troponin-I Utilizing Isoform-Specific Monoclonal Antibodies. *Clin. Biochem.* 29 (4): 301-308 (1996).
Database EMBL Accession No. P02643 1986 XP-002275449.
Filatov et al., "Troponin:Structure, Properties, and Mechansim of Functioning", Biochemistry 1999 64(9) :969-985 XP008028931.
Huang et al., "The Amino Acid Sequences of the Phosphorylated Sites in Troponin-I from Rabbit Skeletal Muscle", FEBS Letters 1974 42(3) :249-252 XP-001188933.
Labugger et al., "Extensive Troponin I and T Modification Detected in Serum From Patients With Acute Myocardial Infarction", Circulation 2000 102:1221-1226 XP-001080442.
Li et al., "Phosphorylation and Mutation of Human Cardiac Troponin I Deferentially Destabilize the Interaction of the Functional Regions of Troponin I with Troponin C", Biochemistry 2003 42:14460-14468 XP-002275176.
Li Monica et al., "Novel Phosphorylation of Ser 149 in Cardiac Troponin I (cTnI) by PAK Reduces the Affinity of cTnI for Cardiac Troponin C (cTnC)", 46th Annual Meeting of the Biophysical Society 2002 p. 389a 1894-Pos XP008028764.
McDonough et al., "Troponin I Degradation and Covalent Complex Formation Accompanies Myocardial Ischemia/Reperfusion Injury", Circ Res 1999 84:9-20 XP002275174.
Moir et al., "The Phosphorylation Sites of Troponin I from White Skeletal Muscle of the Rabbit", FEBS Letters 1974 42(3) :253-256 XP-001189064.
Simpson et al., "Differential Detection of Skeletal Troponin I Isoforms in Serum of a Patient with Rhabdomyolysis:Markers of Muscle Injury?", Clinical Chemistry 2002 48(7) :1112-1114 XP-002275173.
Solaro et al., "Altered Interactions Among Thin Filament Proteins Modulate Cardiac Function", J Mol Cell Cardiol 1996 28(2) :217-230 XP-002275175.

(Continued)

*Primary Examiner*—Karen Cochrane Carlson
(74) *Attorney, Agent, or Firm*—Licata & Tyrrell P.C.

(57) ABSTRACT

Isolated phosphorylated troponin I proteins useful in diagnosing and monitoring the phosphorylation state of injured muscle tissue are provided. Also provided are compounds, kits and methods for assessing the phosphorylation state of these troponin I proteins and modulating the phosphorylation state of these troponin I proteins in a subject.

13 Claims, 9 Drawing Sheets

OTHER PUBLICATIONS

Van Eyk et al., "Cardiac Disease-Induced Post-Translational Modifications of Troponin I:Differential Proteolysis, Phosphorylation and Covalent Complex Formation", 44th Annual Meetinf of the Biophysical Society Feb. 12-16, 2000 632-POS XP008028766.

Wilkinson et al., "The Amino Acid Sequence of Troponin I from Rabbit Skeletal Muscle", Biochem. J. 1975 149:493-496 XP008028897.

Takeishi et al., "In Vivo Phosphorylation of Cardiac Troponin I by Protein Kinase Cβ2 Decreases Cardiomyocyte Calcium Responsiveness and Contractility in Transgenic Mouse Hearts", J. Clin. Invest. 1998 102:72-78.

Andres et al., "Contractile proteins in globally "stunned" rabbit myocardium", Basic Res. Cardiol. 1991 86:219-226.

Chan et al., "Rapid analysis of fatty acid-binding proteins with immunosensors and immunotests for early monitoring of tissue injury", Biosensors and Bioelectronics 2005 20:2566-2580.

Härtner et al., "Fast and slow isoforms of troponin I and troponin c—Distribution in normal rabbit muscles and effects of chronic stimulation", Eur. J. Biochem. 1990 188:261-267.

Konagaya et al., "Increased Serum Myosin Light Chain 3 Level in Neuromusclar Diseases", Muscle & Nerve 1987 10:415-421.

Larue et al., "Immunoradiometric Assay of Myosin Heavy Chain Fragments in Plasma for Investigation of Myocardial Infarction", Clin. Chem. 1991 37/1:78-82.

Morano et al., "Phosphorylation and Thiophosphorylation by Myosin Light Chain Kinase:Different Effects on Mechanical Properties of Chemically Skinned Ventricular Fibers from the Pig", J Mol Cell Cardiol 1990 22:805-813.

Ravkilde, J., "Creatine kinase isoenzyme MB mass, cardiac troponin T, and myosin light chain isotype 1 as serological markers of myocardial injury and their prognostic importance in acute coronary syndrome", Dan. Med. Bull. 1998 45(1):34-50.

Thompson et al., "Signalling Pathways Regulating Protein Turnover in Skeletal Muscle", Cell. Signal. 1998 10(1):1-11.

Wolff et al., "Myofibrillar Calcium Sensitivity of Isometric Tension Is Increased in Human Dilated Cardiomyopathies", J. Clin. Invest. 1996 98:167-176.

Yuasa et al., "A Novel Interaction of cGMP-dependent Protein Kinase I with Troponin T", J. Biol. Chem. 1999 274(52):37429-37434.

U.S. Appl. No. 11/138,184, filed May 26, 2005.
U.S. Appl. No. 09/115,589, filed Jul. 15, 1998.

* cited by examiner

FIGURE 5A-C

```
Human fstnI (121-181)
Human sstnI (122-186)
Human ctnI (153-209)
Chick..fs.MLFALLGSKH KVFMDLRANL KQVKKEDTEK EKDL.RDVGD WRKNIEEKSG MEGRKKMFEAEGES        (SEQ ID NO: 17)
Mouse..fs.MLKALLGSKH KVCMDLRANL KQVKKEDTEK ERDL.RDVGD WRKNIEEKSG MEGRKKMFES ES        (SEQ ID NO: 18)
Human..fs.MLKALLGSKH KVCMDLRANL KQVKKEDTEK ERDL.RDVGD WRKNIEEKSG MEGRKKMFES ES        (SEQ ID NO: 19)
Rat....fs.MLKALLGSKH KVCMDLRANL KQVKKEDTEK ERDL.RDVGD WRKNIEEKSG MEGRKKMFES ES        (SEQ ID NO: 15)
Rabbit.fs.MLKALLGSKH KVCMDLRANL KQVKKEDTEK ERDL.RDVGD WRKNIEEKSG MEGRKKMFES ES        (SEQ ID NO: 20)
HUMAN..ss.MLRALLGSKH KVSMDLRANL KSVKKEDTEK ER..PVVGD  WRKNVEAMSG MEGRKKMFDA AKSPTSQ   (SEQ ID NO: 21)
Rat....ss.MLRALLGSKH KVSMDLRANL KSVKKEDTEK ER..PVVGD  WRKNMEAMSG MEGRKKMFDA AKSPTIQ   (SEQ ID NO: 22)
Rabit..ss.MLRALLGSKH KVSMDLRANL KSVKKEDTEK ER..PVVGD  WRKNMEAMSG MEGRKKMFDA AKSPTSQ   (SEQ ID NO: 23)
HUMAN..c..MMQALLGARA KESLDLRAHL KQVKKEDTEK EN...RVGD  WRKNIDALSG MEGRKKFEG           (SEQ ID NO: 24)
Rabit..c..MMQALLGTRA KETLDLRAHL KQVKKEDTEK EN...REVGD WRKNIDLSG  MEGRKKFEG           (SEQ ID NO: 25)
Rat....c..MMQALLGTRA KESLDLRAHL KQVKKEDIEK EN...REVGD WRKNIDALSG MEGRKKFEG           (SEQ ID NO: 16)
Chick..c..MMAALLGSKH RVGTDLRAGL RQVRKDDAEK ES...REVGD WRKNVDALSG MEGRKKFE PGGGQ      (SEQ ID NO: 26)
Bovin..c..MMQALLGARA KETLDLRAHL KQVKKEDTEK EN...REVGD WRKNIDALSG MEGRKKFEG           (SEQ ID NO: 27)

Human fstnI (101-140)
Human sstnI (102-141)
Human ctnI (133-172)
Chick..fs.DLRGKFKRPP LR..RVRMSAD AMLFALLGSK HKVFMDLRANL     (SEQ ID NO: 30)
Mouse..fs.DLRGKFKRPP LR..RVRMSAD AMLKALLGSK HKVCMDLRANL     (SEQ ID NO: 31)
Human..fs.DLRGKFKRPP LR..RVRMSAD AMLKALLGSK HKVCMDLRANL     (SEQ ID NO: 32)
Rat....fs.DLRGKFKRPP LR..RVRMSAD AMLKALLGSK HKVCMDLRANL     (SEQ ID NO: 28)
Rabbit.fs.DLRGKFKRPP LR..RVRMSAD AMLKALLGSK HKVCMDLRANL     (SEQ ID NO: 33)
HUMAN..ss.DLRGKFKRPP LR..RVRVSAD AMLFALLGSK HKVSMDLRANL     (SEQ ID NO: 34)
RABIT..ss.DLRGKFKRPP LR..RVRVSAD AMLFALLGSK HKVSMDLRANL     (SEQ ID NO: 36)
RAT....ss.DLRGKFKRPP LR..RVRVSAD AMLFALLGSK HKVSMDLRANL     (SEQ ID NO: 35)
HUMAN..c..DLRGKFKRPT LR..RVRISAD AMQALLGTR  AKESDLRAHL      (SEQ ID NO: 37)
MOUSE..c..DLRGKFKRPT LR..RVRISAD AMMQALLGTR AKDSDLRAHL      (SEQ ID NO: 40)
RABIT..c..DLRGKFKRPT LRLRVRISAD AMMQALLGTR  AKETDLRAHL      (SEQ ID NO: 38)
RAT....c..DLRGKFKRPT LR..RVRISAD AMMQALLGTR AKESDLRAHL      (SEQ ID NO: 29)
BOVIN..c..DLRGKFKRPT LR..RVRISAD AMMQALLGAR AKETDLRAHL      (SEQ ID NO: 39)
```

FIGURE 8

SEQUENCE LISTING

```
<160> NUMBER OF SEQ ID NOS: 40

<210> SEQ ID NO 1
<211> LENGTH: 181
<212> TYPE: PRT
<213> ORGANISM: Rattus norvegicus
```

<400> SEQUENCE: 1

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Ser Arg Arg Glu Ser Glu Lys Gln Asn Tyr Leu Ser Glu His Cys
        35                  40                  45

Pro Pro Leu His Ile Pro Gly Ser Met Ser Glu Val Gln Glu Leu Cys
    50                  55                  60

Lys Gln Leu His Ala Lys Ile Asp Ala Ala Glu Glu Lys Tyr Asp
65                  70                  75                  80

Met Glu Val Lys Val Gln Lys Ser Ser Lys Glu Leu Glu Asp Met Asn
                85                  90                  95

Gln Lys Leu Phe Asp Leu Arg Gly Lys Phe Lys Arg Pro Pro Leu Arg
            100                 105                 110

Arg Val Arg Met Ser Ala Asp Ala Met Leu Lys Ala Leu Leu Gly Ser
        115                 120                 125

Lys His Lys Val Cys Met Asp Leu Arg Ala Asn Leu Lys Gln Val Lys
130                 135                 140

Lys Glu Asp Thr Glu Lys Glu Arg Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ser Glu Ser
            180

<210> SEQ ID NO 2
<211> LENGTH: 210
<212> TYPE: PRT
<213> ORGANISM: Rattus norvegicus

<400> SEQUENCE: 2

Ala Asp Glu Ser Ser Asp Ala Ala Gly Glu Pro Gln Pro Ala Pro Ala
1               5                   10                  15

Pro Val Arg Arg Arg Ser Ser Ala Asn Tyr Arg Ala Tyr Ala Thr Glu
            20                  25                  30

Pro His Ala Lys Lys Ser Lys Ile Ser Ala Ser Arg Lys Leu Gln
        35                  40                  45

Leu Lys Thr Leu Met Leu Gln Ile Ala Lys Gln Glu Met Glu Arg Glu
    50                  55                  60

Ala Glu Glu Arg Arg Gly Glu Lys Gly Arg Val Leu Ser Thr Arg Cys
65                  70                  75                  80

Gln Pro Leu Val Leu Asp Gly Leu Gly Phe Glu Leu Gln Asp Leu
            85                  90                  95

Cys Arg Gln Leu His Ala Arg Val Asp Lys Val Asp Glu Glu Arg Tyr
        100                 105                 110

Asp Val Glu Ala Lys Val Thr Lys Asn Ile Thr Glu Ile Ala Asp Leu
    115                 120                 125

Thr Gln Lys Ile Tyr Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Thr Arg Ala Lys Glu Ser Leu Asp Leu Arg Ala His Leu Lys Gln Val
                165                 170                 175

```
Lys Lys Glu Asp Ile Glu Lys Glu Asn Arg Glu Val Gly Asp Trp Arg
            180                 185                 190

Lys Asn Ile Asp Ala Leu Ser Gly Met Glu Gly Arg Lys Lys Phe
        195                 200                 205

Glu Gly
    210

<210> SEQ ID NO 3
<211> LENGTH: 182
<212> TYPE: PRT
<213> ORGANISM: Gallus gallus

<400> SEQUENCE: 3

Ser Asp Glu Glu Lys Lys Arg Arg Ala Thr Ala Arg Arg Gln His
1               5                   10                  15

Leu Lys Ser Ala Met Leu Gln Leu Ala Val Thr Glu Ile Glu Lys Glu
            20                  25                  30

Ala Ala Ala Lys Glu Val Glu Lys Gln Asn Tyr Leu Ala Glu His Cys
            35                  40                  45

Pro Pro Leu Ser Leu Pro Gly Ser Met Gln Glu Leu Gln Glu Leu Cys
        50                  55                  60

Lys Lys Leu His Ala Lys Ile Asp Ser Val Asp Glu Arg Tyr Asp
65              70                  75                  80

Thr Glu Val Lys Leu Gln Lys Thr Asn Lys Glu Leu Glu Asp Leu Ser
                85                  90                  95

Gln Lys Leu Phe Asp Leu Arg Gly Lys Phe Lys Arg Pro Pro Leu Arg
            100                 105                 110

Arg Val Arg Met Ser Ala Asp Ala Met Leu Arg Ala Leu Leu Gly Ser
            115                 120                 125

Lys His Lys Val Asn Met Asp Leu Arg Ala Asn Leu Lys Gln Val Lys
        130                 135                 140

Lys Glu Asp Thr Glu Lys Glu Lys Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ala Gly Glu Ser
            180

<210> SEQ ID NO 4
<211> LENGTH: 181
<212> TYPE: PRT
<213> ORGANISM: Mus musculus

<400> SEQUENCE: 4

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Ser Arg Arg Glu Ser Glu Lys Glu Asn Tyr Leu Ser Glu His Cys
        35                  40                  45

Pro Pro Leu His Ile Pro Gly Ser Met Ser Glu Val Gln Glu Leu Cys
        50                  55                  60

Lys Gln Leu His Ala Lys Ile Asp Val Ala Glu Glu Lys Tyr Asp
65              70                  75                  80

Met Glu Val Lys Val Gln Lys Ser Ser Lys Glu Leu Glu Asp Met Asn
                85                  90                  95
```

```
Gln Lys Leu Phe Asp Leu Arg Gly Lys Phe Lys Arg Pro Pro Leu Arg
            100                 105                 110

Arg Val Arg Met Ser Ala Asp Ala Met Leu Lys Ala Leu Leu Gly Ser
        115                 120                 125

Lys His Lys Val Cys Met Asp Leu Arg Ala Asn Leu Lys Gln Val Lys
130                 135                 140

Lys Glu Asp Thr Glu Lys Glu Arg Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ser Glu Ser
            180

<210> SEQ ID NO 5
<211> LENGTH: 181
<212> TYPE: PRT
<213> ORGANISM: Homo sapien

<400> SEQUENCE: 5

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Ser Arg Arg Glu Ala Glu Lys Gln Asn Tyr Leu Ala Glu His Cys
        35                  40                  45

Pro Pro Leu His Ile Pro Gly Ser Met Ser Glu Val Gln Glu Leu Cys
    50                  55                  60

Lys Gln Leu His Ala Lys Ile Asp Ala Ala Glu Glu Lys Tyr Asp
65                  70                  75                  80

Met Glu Val Arg Val Gln Lys Thr Ser Lys Glu Leu Glu Asp Met Asn
                85                  90                  95

Gln Lys Leu Phe Asp Leu Arg Gly Lys Phe Lys Arg Pro Pro Leu Arg
            100                 105                 110

Arg Val Arg Met Ser Ala Asp Ala Met Leu Lys Ala Leu Leu Gly Ser
        115                 120                 125

Lys His Lys Val Cys Met Asp Leu Arg Ala Asn Leu Lys Gln Val Lys
130                 135                 140

Lys Glu Asp Thr Glu Lys Glu Arg Asp Leu Arg Asp Val Gly Asp Trp
145                 150                 155                 160

Arg Lys Asn Ile Glu Glu Lys Ser Gly Met Glu Gly Arg Lys Lys Met
                165                 170                 175

Phe Glu Ser Glu Ser
            180

<210> SEQ ID NO 6
<211> LENGTH: 181
<212> TYPE: PRT
<213> ORGANISM: Oryctolagus cuniculus

<400> SEQUENCE: 6

Gly Asp Glu Glu Lys Arg Asn Arg Ala Ile Thr Ala Arg Arg Gln His
1               5                   10                  15

Leu Lys Ser Val Met Leu Gln Ile Ala Ala Thr Glu Leu Glu Lys Glu
            20                  25                  30

Glu Gly Arg Arg Glu Ala Glu Lys Gln Asn Tyr Leu Ala Glu His Cys
        35                  40                  45
```

-continued

```
Pro Pro Leu Ser Leu Pro Gly Ser Met Ala Glu Val Gln Glu Leu Cys
    50                  55                  60
Lys Gln Leu His Ala Lys Ile Asp Ala Ala Glu Glu Lys Tyr Asp
 65                 70                  75                  80
Met Glu Ile Lys Val Gln Lys Ser Ser Lys Glu Leu Glu Asp Met Asn
                85                  90                  95
Gln Lys Leu Phe Asp Leu Arg Gly Lys Phe Lys Arg Pro Pro Leu Arg
            100                 105                 110
Arg Val Arg Met Ser Ala Asp Ala Met Leu Lys Ala Leu Leu Gly Ser
        115                 120                 125
Lys His Lys Val Cys Met Asp Leu Arg Ala Asn Leu Lys Gln Val Lys
130                 135                 140
Lys Glu Asp Thr Glu Lys Glu Arg Asp Leu Arg Asp Val Gly Asp Trp
145                 150                 155                 160
Arg Lys Asn Ile Glu Glu Lys Ser Gly Met Glu Gly Arg Lys Lys Met
                165                 170                 175
Phe Glu Ser Glu Ser
            180
```

<210> SEQ ID NO 7
<211> LENGTH: 186
<212> TYPE: PRT
<213> ORGANISM: Homo sapien

<400> SEQUENCE: 7

```
Pro Glu Val Glu Arg Lys Pro Lys Ile Thr Ala Ser Arg Lys Leu Leu
 1               5                  10                  15
Leu Lys Ser Leu Met Leu Ala Lys Ala Lys Glu Cys Trp Glu Gln Glu
                20                  25                  30
His Glu Glu Arg Glu Ala Glu Lys Val Arg Tyr Leu Ala Glu Arg Ile
            35                  40                  45
Pro Thr Leu Gln Thr Arg Gly Leu Ser Leu Ser Ala Leu Gln Asp Leu
        50                  55                  60
Cys Arg Glu Leu His Ala Lys Val Glu Val Asp Glu Glu Arg Tyr
 65                 70                  75                  80
Asp Ile Glu Ala Lys Cys Leu His Asn Thr Arg Glu Ile Lys Asp Leu
                85                  90                  95
Lys Leu Lys Val Met Asp Leu Arg Gly Lys Phe Lys Arg Pro Pro Leu
            100                 105                 110
Arg Arg Val Arg Val Ser Ala Asp Ala Met Leu Arg Ala Leu Leu Gly
        115                 120                 125
Ser Lys His Lys Val Ser Met Asp Leu Arg Ala Asn Leu Lys Ser Val
130                 135                 140
Lys Lys Glu Asp Thr Glu Lys Glu Arg Pro Val Glu Val Gly Asp Trp
145                 150                 155                 160
Arg Lys Asn Val Glu Ala Met Ser Gly Met Glu Gly Arg Lys Lys Met
                165                 170                 175
Phe Asp Ala Ala Lys Ser Pro Thr Ser Gln
            180                 185
```

<210> SEQ ID NO 8
<211> LENGTH: 186
<212> TYPE: PRT
<213> ORGANISM: Rattus norvegicus -continued

```
<400> SEQUENCE: 8

Pro Glu Val Glu Arg Lys Ser Lys Ile Thr Ala Ser Arg Lys Leu Met
1               5                   10                  15

Leu Lys Ser Leu Met Leu Ala Lys Ala Lys Glu Cys Trp Glu Gln Glu
            20                  25                  30

His Glu Glu Arg Glu Ala Glu Lys Val Arg Tyr Leu Ser Glu Arg Ile
        35                  40                  45

Pro Thr Leu Gln Thr Arg Gly Leu Ser Leu Ser Ala Leu Gln Asp Leu
    50                  55                  60

Cys Arg Glu Leu His Ala Lys Val Glu Val Asp Glu Glu Arg Tyr
65                  70                  75                  80

Asp Ile Glu Ala Lys Cys Leu His Asn Thr Arg Glu Ile Lys Asp Leu
                85                  90                  95

Lys Leu Lys Val Leu Asp Leu Arg Gly Lys Phe Lys Arg Pro Pro Leu
            100                 105                 110

Arg Arg Val Arg Val Ser Ala Asp Ala Met Leu Arg Ala Leu Leu Gly
            115                 120                 125

Ser Lys His Lys Val Ser Met Asp Leu Arg Ala Asn Leu Lys Ser Val
    130                 135                 140

Lys Lys Glu Asp Thr Glu Lys Glu Arg Pro Val Glu Val Gly Asp Trp
145                 150                 155                 160

Arg Lys Asn Val Glu Ala Met Ser Gly Met Glu Gly Arg Lys Lys Met
                165                 170                 175

Phe Asp Ala Ala Lys Ser Pro Thr Leu Gln
            180                 185

<210> SEQ ID NO 9
<211> LENGTH: 184
<212> TYPE: PRT
<213> ORGANISM: Oryctologus cuniculus

<400> SEQUENCE: 9

Pro Glu Val Glu Arg Lys Ser Lys Ile Thr Ala Ser Arg Lys Leu Leu
1               5                   10                  15

Lys Ser Leu Met Leu Ala Lys Ala Lys Glu Cys Gln Gln Glu His Glu
            20                  25                  30

Ala Arg Glu Ala Glu Lys Val Arg Tyr Leu Ala Glu Arg Ile Pro Ala
        35                  40                  45

Leu Gln Thr Arg Gly Leu Ser Leu Ser Ala Leu Gln Asp Leu Cys Arg
    50                  55                  60

Gln Leu His Ala Lys Val Glu Val Val Asp Glu Glu Arg Tyr Asp Ile
65                  70                  75                  80

Glu Ala Lys Cys Leu His Asn Thr Arg Glu Ile Lys Asp Leu Lys Leu
                85                  90                  95

Lys Val Leu Asp Leu Arg Gly Lys Phe Lys Arg Pro Pro Leu Arg Arg
            100                 105                 110

Val Arg Val Ser Ala Asp Ala Met Leu Arg Ala Leu Leu Gly Ser Lys
            115                 120                 125

His Lys Val Ser Met Asp Leu Arg Ala Asn Leu Lys Ser Val Lys Lys
    130                 135                 140

Glu Asp Thr Glu Lys Glu Arg Pro Val Glu Val Gly Asp Trp Arg Lys
145                 150                 155                 160
```

-continued

Asn Val Glu Ala Met Ser Gly Met Glu Gly Arg Lys Met Phe Asp
            165                 170                 175

Ala Ala Lys Ser Pro Thr Ser Gln
            180

<210> SEQ ID NO 10
<211> LENGTH: 209
<212> TYPE: PRT
<213> ORGANISM: Homo sapien

<400> SEQUENCE: 10

Ala Asp Gly Ser Ser Asp Ala Ala Arg Glu Pro Arg Pro Ala Pro Ala
1               5                   10                  15

Pro Ile Arg Arg Arg Ser Ser Asn Tyr Arg Ala Tyr Ala Thr Glu Pro
            20                  25                  30

His Ala Lys Lys Ser Lys Ile Ser Ala Ser Arg Lys Leu Gln Leu
            35                  40                  45

Lys Thr Leu Leu Leu Gln Ile Ala Lys Gln Glu Leu Glu Arg Glu Ala
    50                  55                  60

Glu Glu Arg Arg Gly Glu Lys Gly Arg Ala Leu Ser Thr Arg Cys Gln
65                  70                  75                  80

Pro Leu Glu Leu Ala Gly Leu Gly Phe Ala Glu Leu Gln Asp Leu Cys
                85                  90                  95

Arg Gln Leu His Ala Arg Val Asp Lys Val Asp Glu Arg Tyr Asp
            100                 105                 110

Ile Glu Ala Lys Val Thr Lys Asn Ile Thr Glu Ile Ala Asp Leu Thr
            115                 120                 125

Gln Lys Ile Phe Asp Leu Arg Gly Lys Phe Lys Arg Pro Thr Leu Arg
    130                 135                 140

Arg Val Arg Ile Ser Ala Asp Ala Met Met Gln Ala Leu Leu Gly Ala
145                 150                 155                 160

Arg Ala Lys Glu Ser Leu Asp Leu Arg Ala His Leu Lys Gln Val Lys
                165                 170                 175

Lys Glu Asp Thr Glu Lys Glu Asn Arg Glu Val Gly Asp Trp Arg Lys
            180                 185                 190

Asn Ile Asp Ala Leu Ser Gly Met Glu Gly Arg Lys Lys Lys Phe Glu
            195                 200                 205

Ser

<210> SEQ ID NO 11
<211> LENGTH: 206
<212> TYPE: PRT
<213> ORGANISM: Oryctologus cuniculus

<400> SEQUENCE: 11

Ala Asp Glu Ser Arg Asp Ala Ala Gly Glu Ala Arg Pro Ala Pro Ala
1               5                   10                  15

Val Arg Arg Ser Asp Arg Ala Tyr Ala Thr Glu Pro His Ala Lys Ser
            20                  25                  30

Lys Lys Lys Ile Ser Ala Ser Arg Lys Leu Gln Leu Lys Thr Leu Met
            35                  40                  45

Leu Gln Ile Ala Lys Gln Glu Leu Glu Arg Glu Ala Glu Glu Arg Arg
    50                  55                  60

Gly Glu Lys Gly Arg Ala Leu Ser Thr Arg Cys Gln Pro Leu Glu Leu
65                  70                  75                  80

```
Ala Gly Leu Gly Phe Ala Glu Leu Gln Asp Leu Cys Arg Gln Leu His
                85                  90                  95

Ala Arg Val Asp Lys Val Asp Glu Arg Tyr Asp Val Glu Ala Lys
            100                 105                 110

Val Thr Lys Asn Ile Thr Glu Ile Ala Asp Leu Thr Gln Lys Ile Phe
        115                 120                 125

Asp Leu Arg Gly Lys Phe Lys Arg Pro Thr Leu Arg Leu Arg Val Arg
        130                 135                 140

Ile Ser Ala Asp Ala Met Met Gln Ala Leu Leu Gly Thr Arg Ala Lys
145                 150                 155                 160

Glu Thr Leu Asp Leu Arg Ala His Leu Lys Gln Val Lys Lys Glu Asp
                165                 170                 175

Thr Glu Lys Glu Asn Arg Glu Val Gly Asp Trp Arg Lys Asn Ile Asp
            180                 185                 190

Leu Leu Ser Gly Met Glu Gly Arg Lys Lys Lys Phe Glu Gly
        195                 200                 205

<210> SEQ ID NO 12
<211> LENGTH: 168
<212> TYPE: PRT
<213> ORGANISM: Gallus gallus

<400> SEQUENCE: 12

Lys Leu Gln Leu Lys Thr Leu Leu Leu Gln Arg Ala Lys Arg Glu Leu
1               5                   10                  15

Glu Arg Glu Glu Gln Arg Ala Gly Glu Lys Gln Arg His Leu Gly
            20                  25                  30

Gly Leu Cys Pro Pro Glu Leu Glu Gly Leu Gly Val Ala Gln Leu
        35                  40                  45

Gln Glu Leu Cys Arg Glu Leu His Ala Arg Ile Ala Val Asp Glu Glu
    50                  55                  60

Arg Tyr Asp Met Gly Thr Arg Val Ser Lys Asn Met Ala Glu Met Glu
65                  70                  75                  80

Glu Leu Arg Arg Arg Val Ala Gly Gly Arg Phe Val Arg Pro Ala Leu
                85                  90                  95

Arg Arg Val Arg Leu Ser Ala Asp Ala Met Met Ala Leu Leu Gly
            100                 105                 110

Ser Lys His Arg Val Gly Thr Asp Leu Arg Ala Gly Leu Arg Gln Val
        115                 120                 125

Arg Lys Asp Asp Ala Glu Lys Glu Ser Arg Glu Val Gly Asp Trp Arg
        130                 135                 140

Lys Asn Val Asp Ala Leu Ser Gly Met Glu Gly Arg Lys Lys Lys Phe
145                 150                 155                 160

Glu Ala Pro Gly Gly Gly Gln Gly
                165

<210> SEQ ID NO 13
<211> LENGTH: 211
<212> TYPE: PRT
<213> ORGANISM: Bos taurus

<400> SEQUENCE: 13

Ala Asp Arg Ser Gly Gly Ser Thr Ala Gly Asp Thr Val Pro Ala Pro
1               5                   10                  15

Pro Pro Val Arg Arg Arg Ser Ser Ala Asn Tyr Arg Ala Tyr Ala Thr
            20                  25                  30
```

```
Glu Pro His Ala Lys Lys Ser Lys Ile Ser Ala Ser Arg Lys Leu
            35                  40                  45

Gln Leu Lys Thr Leu Met Leu Gln Ile Ala Lys Gln Glu Leu Glu Arg
     50                  55                  60

Glu Ala Glu Arg Arg Gly Glu Lys Gly Arg Ala Leu Ser Thr Arg
 65              70                  75                  80

Cys Gln Pro Leu Glu Leu Ala Gly Leu Gly Phe Ala Glu Leu Gln Asp
                    85                  90                  95

Leu Cys Arg Gln Leu His Ala Arg Val Asp Lys Val Asp Glu Glu Arg
                100                 105                 110

Tyr Asp Val Glu Ala Lys Val Thr Lys Asn Ile Thr Glu Ile Ala Asp
                115                 120                 125

Leu Asn Gln Lys Ile Phe Asp Leu Arg Gly Lys Phe Lys Arg Pro Thr
        130                 135                 140

Leu Arg Arg Val Arg Ile Ser Ala Asp Ala Met Met Gln Ala Leu Leu
145                 150                 155                 160

Gly Ala Arg Ala Lys Glu Thr Leu Asp Leu Arg Ala His Leu Lys Gln
                165                 170                 175

Val Lys Lys Glu Asp Thr Glu Lys Glu Asn Arg Glu Val Gly Asp Trp
        180                 185                 190

Arg Lys Asn Ile Asp Ala Leu Ser Gly Met Glu Gly Arg Lys Lys Lys
                195                 200                 205

Phe Glu Gly
        210

<210> SEQ ID NO 14
<211> LENGTH: 210
<212> TYPE: PRT
<213> ORGANISM: Mus musculus

<400> SEQUENCE: 14

Ala Asp Glu Ser Ser Asp Ala Ala Gly Glu Pro Gln Pro Ala Pro Ala
 1               5                  10                  15

Pro Val Arg Arg Arg Ser Ser Ala Asn Tyr Arg Ala Tyr Ala Thr Glu
            20                  25                  30

Pro His Ala Lys Lys Ser Lys Ile Ser Ala Ser Arg Lys Leu Gln
                35                  40                  45

Leu Lys Thr Leu Met Leu Gln Ile Ala Lys Gln Glu Met Glu Arg Glu
     50                  55                  60

Ala Glu Arg Arg Gly Glu Lys Gly Arg Val Leu Arg Thr Arg Cys
 65              70                  75                  80

Gln Pro Leu Glu Leu Asp Gly Leu Gly Phe Glu Glu Leu Gln Asp Leu
                    85                  90                  95

Cys Arg Gln Leu His Ala Arg Val Asp Lys Val Asp Glu Glu Arg Tyr
                100                 105                 110

Asp Val Glu Ala Lys Val Thr Lys Asn Ile Thr Glu Ile Ala Asp Leu
                115                 120                 125

Thr Gln Lys Ile Tyr Asp Leu Arg Gly Lys Phe Lys Arg Pro Thr Leu
        130                 135                 140

Arg Arg Val Arg Ile Ser Ala Asp Ala Met Met Gln Ala Leu Leu Gly
145                 150                 155                 160

Thr Arg Ala Lys Glu Ser Leu Asp Leu Arg Ala His Leu Lys Gln Val
                165                 170                 175

Lys Lys Glu Asp Ile Glu Lys Glu Asn Arg Glu Val Gly Asp Trp Arg
                180                 185                 190
```

```
Lys Asn Ile Asp Ala Leu Ser Gly Met Glu Gly Arg Lys Lys Phe
        195                 200                 205

Glu Gly
    210

<210> SEQ ID NO 15
<211> LENGTH: 61
<212> TYPE: PRT
<213> ORGANISM: Rattus norvegicus

<400> SEQUENCE: 15

Met Leu Lys Ala Leu Leu Gly Ser Lys His Lys Val Cys Met Asp Leu
1               5                   10                  15

Arg Ala Asn Leu Lys Gln Val Lys Lys Glu Asp Thr Glu Lys Glu Arg
            20                  25                  30

Asp Leu Arg Asp Val Gly Asp Trp Arg Lys Asn Ile Glu Glu Lys Ser
        35                  40                  45

Gly Met Glu Gly Arg Lys Lys Met Phe Glu Ser Glu Ser
    50                  55                  60

<210> SEQ ID NO 16
<211> LENGTH: 57
<212> TYPE: PRT
<213> ORGANISM: Rattus norvegicus

<400> SEQUENCE: 16

Met Met Gln Ala Leu Leu Gly Thr Arg Ala Lys Glu Ser Leu Asp Leu
1               5                   10                  15

Arg Ala His Leu Lys Gln Val Lys Lys Glu Asp Ile Glu Lys Glu Asn
            20                  25                  30

Arg Glu Val Gly Asp Trp Arg Lys Asn Ile Asp Ala Leu Ser Gly Met
        35                  40                  45

Glu Gly Arg Lys Lys Lys Phe Glu Gly
    50                  55

<210> SEQ ID NO 17
<211> LENGTH: 62
<212> TYPE: PRT
<213> ORGANISM: Gallus gallus

<400> SEQUENCE: 17

Met Leu Arg Ala Leu Leu Gly Ser Lys His Lys Val Asn Met Asp Leu
1               5                   10                  15

Arg Ala Asn Leu Lys Gln Val Lys Lys Glu Asp Thr Glu Lys Glu Lys
            20                  25                  30

Asp Leu Arg Asp Val Gly Asp Trp Arg Lys Asn Ile Glu Glu Lys Ser
        35                  40                  45

Gly Met Glu Gly Arg Lys Lys Met Phe Glu Ala Gly Glu Ser
    50                  55                  60

<210> SEQ ID NO 18
<211> LENGTH: 61
<212> TYPE: PRT
<213> ORGANISM: Mus musculus

<400> SEQUENCE: 18

Met Leu Lys Ala Leu Leu Gly Ser Lys His Lys Val Cys Met Asp Leu
1               5                   10                  15

Arg Ala Asn Leu Lys Gln Val Lys Lys Glu Asp Thr Glu Lys Glu Arg
            20                  25                  30
```

```
Asp Leu Arg Asp Val Gly Asp Trp Arg Lys Asn Ile Glu Glu Lys Ser
        35                  40                  45

Gly Met Glu Gly Arg Lys Lys Met Phe Glu Ser Glu Ser
    50                  55                  60

<210> SEQ ID NO 19
<211> LENGTH: 61
<212> TYPE: PRT
<213> ORGANISM: Homo sapien

<400> SEQUENCE: 19

Met Leu Lys Ala Leu Leu Gly Ser Lys His Lys Val Cys Met Asp Leu
1               5                   10                  15

Arg Ala Asn Leu Lys Gln Val Lys Lys Glu Asp Thr Glu Lys Glu Arg
            20                  25                  30

Asp Leu Arg Asp Val Gly Asp Trp Arg Lys Asn Ile Glu Glu Lys Ser
        35                  40                  45

Gly Met Glu Gly Arg Lys Lys Met Phe Glu Ser Glu Ser
    50                  55                  60

<210> SEQ ID NO 20
<211> LENGTH: 61
<212> TYPE: PRT
<213> ORGANISM: Oryctolagus cuniculus

<400> SEQUENCE: 20

Met Leu Lys Ala Leu Leu Gly Ser Lys His Lys Val Cys Met Asp Leu
1               5                   10                  15

Arg Ala Asn Leu Lys Gln Val Lys Lys Glu Asp Thr Glu Lys Glu Arg
            20                  25                  30

Asp Leu Arg Asp Val Gly Asp Trp Arg Lys Asn Ile Glu Glu Lys Ser
        35                  40                  45

Gly Met Glu Gly Arg Lys Lys Met Phe Glu Ser Glu Ser
    50                  55                  60

<210> SEQ ID NO 21
<211> LENGTH: 65
<212> TYPE: PRT
<213> ORGANISM: Homo sapien

<400> SEQUENCE: 21

Met Leu Arg Ala Leu Leu Gly Ser Lys His Lys Val Ser Met Asp Leu
1               5                   10                  15

Arg Ala Asn Leu Lys Ser Val Lys Lys Glu Asp Thr Glu Lys Glu Arg
            20                  25                  30

Pro Val Glu Val Gly Asp Trp Arg Lys Asn Val Glu Ala Met Ser Gly
        35                  40                  45

Met Glu Gly Arg Lys Lys Met Phe Asp Ala Ala Lys Ser Pro Thr Ser
    50                  55                  60

Gln
65

<210> SEQ ID NO 22
<211> LENGTH: 65
<212> TYPE: PRT
<213> ORGANISM: Rattus norvegicus
```

-continued

```
<400> SEQUENCE: 22

Met Leu Arg Ala Leu Leu Gly Ser Lys His Lys Val Ser Met Asp Leu
1               5                   10                  15

Arg Ala Asn Leu Lys Ser Val Lys Lys Glu Asp Thr Glu Lys Glu Arg
            20                  25                  30

Pro Val Glu Val Gly Asp Trp Arg Lys Asn Val Glu Ala Met Ser Gly
        35                  40                  45

Met Glu Gly Arg Lys Lys Met Phe Asp Ala Ala Lys Ser Pro Thr Leu
    50                  55                  60

Gln
65

<210> SEQ ID NO 23
<211> LENGTH: 65
<212> TYPE: PRT
<213> ORGANISM: Oryctologus cuniculus

<400> SEQUENCE: 23

Met Leu Arg Ala Leu Leu Gly Ser Lys His Lys Val Ser Met Asp Leu
1               5                   10                  15

Arg Ala Asn Leu Lys Ser Val Lys Lys Glu Asp Thr Glu Lys Glu Arg
            20                  25                  30

Pro Val Glu Val Gly Asp Trp Arg Lys Asn Val Glu Ala Met Ser Gly
        35                  40                  45

Met Glu Gly Arg Lys Lys Met Phe Asp Ala Ala Lys Ser Pro Thr Ser
    50                  55                  60

Gln
65

<210> SEQ ID NO 24
<211> LENGTH: 57
<212> TYPE: PRT
<213> ORGANISM: Homo sapien

<400> SEQUENCE: 24

Met Met Gln Ala Leu Leu Gly Ala Arg Ala Lys Glu Ser Leu Asp Leu
1               5                   10                  15

Arg Ala His Leu Lys Gln Val Lys Lys Glu Asp Thr Glu Lys Glu Asn
            20                  25                  30

Arg Glu Val Gly Asp Trp Arg Lys Asn Ile Asp Ala Leu Ser Gly Met
        35                  40                  45

Glu Gly Arg Lys Lys Lys Phe Glu Ser
    50                  55

<210> SEQ ID NO 25
<211> LENGTH: 57
<212> TYPE: PRT
<213> ORGANISM: Oryctologus cuniculus

<400> SEQUENCE: 25

Met Met Gln Ala Leu Leu Gly Thr Arg Ala Lys Glu Thr Leu Asp Leu
1               5                   10                  15

Arg Ala His Leu Lys Gln Val Lys Lys Glu Asp Thr Glu Lys Glu Asn
            20                  25                  30

Arg Glu Val Gly Asp Trp Arg Lys Asn Ile Asp Leu Leu Ser Gly Met
        35                  40                  45

Glu Gly Arg Lys Lys Lys Phe Glu Gly
    50                  55
```

-continued

<210> SEQ ID NO 26
<211> LENGTH: 63
<212> TYPE: PRT
<213> ORGANISM: Gallus gallus

<400> SEQUENCE: 26

Met Met Ala Ala Leu Leu Gly Ser Lys His Arg Val Gly Thr Asp Leu
1               5                   10                  15

Arg Ala Gly Leu Arg Gln Val Arg Lys Asp Asp Ala Glu Lys Glu Ser
                20                  25                  30

Arg Glu Val Gly Asp Trp Arg Lys Asn Val Asp Ala Leu Ser Gly Met
            35                  40                  45

Glu Gly Arg Lys Lys Lys Phe Glu Ala Pro Gly Gly Gln Gly
        50                  55                  60

<210> SEQ ID NO 27
<211> LENGTH: 57
<212> TYPE: PRT
<213> ORGANISM: Bos taurus

<400> SEQUENCE: 27

Met Met Gln Ala Leu Leu Gly Ala Arg Ala Lys Glu Thr Leu Asp Leu
1               5                   10                  15

Arg Ala His Leu Lys Gln Val Lys Lys Glu Asp Thr Glu Lys Glu Asn
                20                  25                  30

Arg Glu Val Gly Asp Trp Arg Lys Asn Ile Asp Ala Leu Ser Gly Met
            35                  40                  45

Glu Gly Arg Lys Lys Lys Phe Glu Gly
        50                  55

<210> SEQ ID NO 28
<211> LENGTH: 40
<212> TYPE: PRT
<213> ORGANISM: Rattus norvegicus

<400> SEQUENCE: 28

Asp Leu Arg Gly Lys Phe Lys Arg Pro Pro Leu Arg Arg Val Arg Met
1               5                   10                  15

Ser Ala Asp Ala Met Leu Lys Ala Leu Leu Gly Ser Lys His Lys Val
                20                  25                  30

Cys Met Asp Leu Arg Ala Asn Leu
            35                  40

<210> SEQ ID NO 29
<211> LENGTH: 40
<212> TYPE: PRT
<213> ORGANISM: Rattus norvegicus

<400> SEQUENCE: 29

Asp Leu Arg Gly Lys Phe Lys Arg Pro Thr Leu Arg Arg Val Arg Ile
1               5                   10                  15

Ser Ala Asp Ala Met Met Gln Ala Leu Leu Gly Thr Arg Ala Lys Glu
                20                  25                  30

Ser Leu Asp Leu Arg Ala His Leu
            35                  40

<210> SEQ ID NO 30
<211> LENGTH: 40
<212> TYPE: PRT
<213> ORGANISM: Gallus gallus -continued

```
<400> SEQUENCE: 30

Asp Leu Arg Gly Lys Phe Lys Arg Pro Pro Leu Arg Arg Val Arg Met
1               5                   10                  15

Ser Ala Asp Ala Met Leu Arg Ala Leu Leu Gly Ser Lys His Lys Val
            20                  25                  30

Asn Met Asp Leu Arg Ala Asn Leu
        35                  40

<210> SEQ ID NO 31
<211> LENGTH: 40
<212> TYPE: PRT
<213> ORGANISM: Mus musculus

<400> SEQUENCE: 31

Asp Leu Arg Gly Lys Phe Lys Arg Pro Pro Leu Arg Arg Val Arg Met
1               5                   10                  15

Ser Ala Asp Ala Met Leu Lys Ala Leu Leu Gly Ser Lys His Lys Val
            20                  25                  30

Cys Met Asp Leu Arg Ala Asn Leu
        35                  40

<210> SEQ ID NO 32
<211> LENGTH: 40
<212> TYPE: PRT
<213> ORGANISM: Homo sapien

<400> SEQUENCE: 32

Asp Leu Arg Gly Lys Phe Lys Arg Pro Pro Leu Arg Arg Val Arg Met
1               5                   10                  15

Ser Ala Asp Ala Met Leu Lys Ala Leu Leu Gly Ser Lys His Lys Val
            20                  25                  30

Cys Met Asp Leu Arg Ala Asn Leu
        35                  40

<210> SEQ ID NO 33
<211> LENGTH: 40
<212> TYPE: PRT
<213> ORGANISM: Oryctolagus cuniculus

<400> SEQUENCE: 33

Asp Leu Arg Gly Lys Phe Lys Arg Pro Pro Leu Arg Arg Val Arg Met
1               5                   10                  15

Ser Ala Asp Ala Met Leu Lys Ala Leu Leu Gly Ser Lys His Lys Val
            20                  25                  30

Cys Met Asp Leu Arg Ala Asn Leu
        35                  40

<210> SEQ ID NO 34
<211> LENGTH: 40
<212> TYPE: PRT
<213> ORGANISM: Homo sapien

<400> SEQUENCE: 34

Asp Leu Arg Gly Lys Phe Lys Arg Pro Pro Leu Arg Arg Val Arg Val
1               5                   10                  15

Ser Ala Asp Ala Met Leu Arg Ala Leu Leu Gly Ser Lys His Lys Val
            20                  25                  30

Ser Met Asp Leu Arg Ala Asn Leu
        35                  40
```

```
<210> SEQ ID NO 35
<211> LENGTH: 40
<212> TYPE: PRT
<213> ORGANISM: Rattus norvegicus

<400> SEQUENCE: 35

Asp Leu Arg Gly Lys Phe Lys Arg Pro Pro Leu Arg Arg Val Arg Val
1               5                   10                  15

Ser Ala Asp Ala Met Leu Arg Ala Leu Leu Gly Ser Lys His Lys Val
            20                  25                  30

Ser Met Asp Leu Arg Ala Asn Leu
        35                  40

<210> SEQ ID NO 36
<211> LENGTH: 40
<212> TYPE: PRT
<213> ORGANISM: Oryctologus cuniculus

<400> SEQUENCE: 36

Asp Leu Arg Gly Lys Phe Lys Arg Pro Pro Leu Arg Arg Val Arg Val
1               5                   10                  15

Ser Ala Asp Ala Met Leu Arg Ala Leu Leu Gly Ser Lys His Lys Val
            20                  25                  30

Ser Met Asp Leu Arg Ala Asn Leu
        35                  40

<210> SEQ ID NO 37
<211> LENGTH: 40
<212> TYPE: PRT
<213> ORGANISM: Homo sapien

<400> SEQUENCE: 37

Asp Leu Arg Gly Lys Phe Lys Arg Pro Thr Leu Arg Arg Val Arg Ile
1               5                   10                  15

Ser Ala Asp Ala Met Met Gln Ala Leu Leu Gly Ala Arg Ala Lys Glu
            20                  25                  30

Ser Leu Asp Leu Arg Ala His Leu
        35                  40

<210> SEQ ID NO 38
<211> LENGTH: 41
<212> TYPE: PRT
<213> ORGANISM: Oryctologus cuniculus

<400> SEQUENCE: 38

Asp Leu Arg Gly Lys Phe Lys Arg Pro Thr Leu Arg Leu Arg Val Arg
1               5                   10                  15

Ile Ser Ala Asp Ala Met Met Gln Ala Leu Leu Gly Thr Arg Ala Lys
            20                  25                  30

Glu Thr Leu Asp Leu Arg Ala His Leu
        35                  40

<210> SEQ ID NO 39
<211> LENGTH: 40
<212> TYPE: PRT
<213> ORGANISM: Bos taurus
```

```
-continued

<400> SEQUENCE: 39

Asp Leu Arg Gly Lys Phe Lys Arg Pro Thr Leu Arg Arg Val Arg Ile
1               5                   10                  15

Ser Ala Asp Ala Met Met Gln Ala Leu Leu Gly Ala Arg Ala Lys Glu
            20                  25                  30

Thr Leu Asp Leu Arg Ala His Leu
        35                  40

<210> SEQ ID NO 40
<211> LENGTH: 40
<212> TYPE: PRT
<213> ORGANISM: Mus musculus

<400> SEQUENCE: 40

Asp Leu Arg Gly Lys Phe Lys Arg Pro Thr Leu Arg Arg Val Arg Ile
1               5                   10                  15

Ser Ala Asp Ala Met Met Gln Ala Leu Leu Gly Thr Arg Ala Lys Glu
            20                  25                  30

Ser Leu Asp Leu Arg Ala His Leu
        35                  40
```

ISOLATED POST-TRANSLATIONALLY MODIFIED MAMMALIAN PROTEINS FOR MONITORING AND DIAGNOSING MUSCLE DAMAGE

FIELD OF THE INVENTION

This invention relates to isolated post-translationally modified mammalian proteins useful in diagnosing and monitoring injury of skeletal and cardiac muscle.

BACKGROUND OF THE INVENTION

The myofilament subproteome contains both structural and contractile proteins. The thick and thin filament comprise the contractile elements. The thick filament is composed primarily of myosin heavy chain and associated light chains, while the thin filament is composed primarily of actin, tropomyosin (Tm), and the troponin complex (Tn). The Tn complex consists of troponin I (TnI), termed the inhibitory protein due to its ability to block actin-myosin interactions, troponin T (TnT), named for its extensive binding to Tm, and troponin C (TnC) which binds $Ca^{2+}$ and triggers contraction. The binding of $Ca^{2+}$ to the low affinity $Ca^{2+}$-binding sites on TnC results in numerous structural changes that allow the cyclic attachment and detachment of myosin to actin and the subsequent production of force at the expense of ATP hydrolysis (for review see Gordon et al. 2000, *Physiol. Rev.* 80:853–924 and Tobacman, L. S. 1996, *Annu. Rev. Physiol.* 58:447–481).

Alterations to the myofilament protein including, but not limited to, de novo expression, up-regulation of selected proteins, down-regulation of selection proteins, mutations, isoform changes and post-translational modifications have been implicated in a variety of diseases, disorders and/or states of injury.

For example, in cardiac muscle specific and selective modification of cardiac troponin I has been proposed as a molecular mechanism that underlies the contractile dysfunction observed in stunning, and other mild reversible forms of ischemia/reperfusion injury (Bolli et al. 1999, *Phys. Reviews* 79:609–634; McDonough et al. 1999, *Circ. Res.* 84:9–20; Van Eyk et al. 1998, *Circ. Res.* 82:261–271; Foster et al. 1999, *Circ. Res.* 85:470–472; Solaro et al. 1999, *Circ. Res.* 84:122–124). Protein kinase A, C and G have been shown to collectively phosphorylate cardiac troponin I at five different sites (for review see Biochemistry (Mosc) 1999 64(9): 969–85). Further, detection and quantification of cardiac troponin I in serum of patients suffering from acute coronary syndromes has become the most specific and sensitive biochemical marker available for myocardial injury, due to release of the cardiac-specific isoform. Low levels of this protein have also been observed in stable and unstable angina and heart failure.

Mutations in genes encoding skeletal myofilament proteins have been associated with nemaline myopathy, an inherited disorder causing nonprogressive muscle weakness. To date, all identified mutations causing nemaline myopathy and familial hypertrophic cardiomyopathy, an inherited disorder affecting skeletal muscle and heart, respectively, occur within the structural and contractile proteins, as opposed to membrane cytosolic and mitochondrial proteins (Ilkovski et al. 2001 *Am. J. Hum. Genet.* 68:1333–1343; Michele et al. 2000 *J. Mol. Med.* 78:543–553; Shaw et al. 2000 *Lancet* 360(9334):654–5; Bonne et al. 1998 *Circ. Res.* 83(6):580–93; Marian, A. J. 2002 *Curr. Opin. Cardiol.* 17(3):242–52).

In diseases such as chronic obstructive pulmonary disease and congestive heart failure, fiber type switching occurs in skeletal muscle. The nature of the switch is dependent upon the muscle group, namely limb versus respiratory. For example, in chronic obstructive pulmonary disease, the diaphragm, which is in continuous use, has an increased proportion of slow oxidative fatigue-resistant fibers (for review see Gayan-Ramirez and Decramer 1996, *Rev. Mal. Respir.* 17:574–584; Levine et al. 2001, *Exerc. Sport Sci. Rev.* 29:71–75; Stassijns et al. 1996 *Eur. Respir. J.* 9:2161–2187), whereas limb muscles have an increased proportion of fast glycolytic fibers (for review see Aliverti and Macklem 2001 *Respiration* 68:229–239; American Thoracic Society and European Thoracic Society 1991 *Am. J. Respir. Crit. Care Med.* 159:S1–S40; Mador and Bozkanat 2001 *Respir. Res.* 2:216–224; Maltais et al. 2000 *Clin. Chest Med.* 21:5665–677). Fiber-type switching can also be induced during training, for example, in athletes.

Proteolysis of skeletal troponin I has been reported to occur in the diaphragms of severely hypoxemic dogs (Simpson et al. 2000, *J. Appl. Physiol.* 88:753–760). Further, proteolytic fragments of fast and slow skeletal troponin I were detected in serum samples of a patient with rhabdomyolysis (Simpson et al. 2002, *Clin. Chem.* 48:1112–1114). These results are suggestive of skeletal myofilament proteins being susceptible to post-translational modifications.

The detection of intact myofilament proteins, degradation products of myofilament proteins, and protein-protein complexes of myofilament proteins, in various biological samples such as blood, tissue, and urine, was described in detail in U.S. patent application Ser. No. 09/115,589, filed Jul. 15, 1998.

Methods for detection of chemical adducts of myofilament proteins (e.g., post-translational modifications) and various modifications thereof, including protein-protein complexes and protein fragments thereof, were described in detail in U.S. patent application Ser. No. 09/419,901, filed Oct. 18, 1999.

The present invention relates to the identification of post-translationally modified myofilament proteins, and in particular phosphorylated troponin I proteins. The phosphorylation state of troponin I proteins is associated with altered contractile function.

SUMMARY OF THE INVENTION

The present invention provides isolated post-translationally modified mammalian myofilament proteins. In particular, two novel conserved phosphorylation sites have been identified on fast skeletal troponin I and one equivalent phosphorylation site on cardiac troponin I has been identified. These phosphorylation sites are at the C terminus and adjacent to the minimal inhibitory region located in the central region of isoforms of the troponin I protein. The phosphorylation state of troponin I at one or two of these sites is associated with altered contractile function.

Accordingly, an aspect of the present invention is to provide isolated phosphorylated myofilament proteins associated with altered contractile function. In a preferred embodiment, the isolated phosphorylated myofilament protein comprises a phosphorylated isoform of troponin I. More preferred is an isoform of troponin I phosphorylated at its C terminus and/or adjacent to the minimal inhibitory region located at the center of the protein.

Another aspect of the present invention is to provide antibodies and/or aptamers capable of distinguishing between native troponin I and mono and/or diphosphorylated forms of troponin I. Preferred are antibodies and/or aptamers capable of distinguishing between native troponin I and troponin I phosphorylated at its C terminus and/or adjacent to the minimal inhibitory region. Also preferred are antibodies and/or aptamers capable of distinguishing between a native troponin I isoform and a mono and/or diphosphorylated isoform thereof.

Another aspect of the present invention relates to kits and methods for detecting the phosphorylation state of troponin I. In a preferred embodiment, the kits and methods detect troponin I phosphorylated at its C terminus and/or adjacent to its minimal inhibitory region. Also preferred are kits and methods which can distinguish phosphorylated isoforms of troponin I. The kits and methods of the present invention are useful in monitoring and/or diagnosing injury of skeletal and cardiac muscle and altered contractile function of cardiac and skeletal muscle.

In accordance with the invention, the phosphorylation state of troponin I in a biological sample is determined. The biological sample can be obtained from any subject exhibiting, exposed to, suspected of having, or being treated for, a condition or conditions which could cause injury to muscle tissue.

Accordingly, determination of the phosphorylation state of troponin I can be used to monitor subjects with damaged cardiac muscle (e.g. resulting from heart failure or angina) and/or skeletal muscle. Further, monitoring of the phosphorylation state in a subject can be used prognostically to predict acute events such a myocardial infarction.

The invention further provides for the assessment of therapies for muscle damage through monitoring of changes in the phosphorylation state of troponin I upon administration of the therapy. The appropriateness of the level of training and/or enhancement performing drugs in athletes and animals such as race horses can also be assessed by monitoring the phosphorylation state of troponin I in these subjects.

Another aspect of the invention relates to a composition comprising an agent targeted to a phosphatase and/or kinase which alters the phosphorylation state of troponin I and a method for modulating the phosphorylation state of troponin I via administration of this composition. Such compositions alter the calcium sensitivity of muscle tissue and/or the contractility of muscle tissue in a subject and are expected to be useful in the treatment of muscle injury.

Other features and advantages of the invention will be apparent from the following detailed description, and from the claims.

BRIEF DESCRIPTION OF THE DRAWINGS

Embodiments of the invention will now be described, by way of example, with reference to the accompanying drawings, wherein:

FIG. 8 shows a comparison of the conserved serine sites for phosphorylation in isoforms of troponin I from various mammals. Shown is a comparison of amino acid sequences of the region of the C terminus for fast skeletal troponin I from chick (Swiss Prot P02644; full length shown in SEQ ID NO:3; fragment shown in the SEQ ID NO:17),. mouse (Swiss Prot P13412; full length shown in SEQ ID NO:4; fragment shown in SEQ ID NO:18), human (Swiss Prot P48788; full length shown in SEQ ID NO:5; fragment shown in SEQ ID NO:19), rat (Swiss Prot P27768; full length shown in SEQ ID NO:1; fragment shown in SEQ ID NO:15) and rabbit (Swiss Prot P02643; full length shown in SEQ ID NO:6; fragment shown in SEQ ID NO:20), slow skeletal troponin I from human (Swiss Prot P19237; full length shown in SEQ ID NO:7; fragment shown in SEQ ID NO:21), rat (Swiss Prot P13413; full length shown in SEQ ID NO:8; fragment shown in SEQ ID NO:22) and rabbit (Swiss Prot P02645; full length shown in SEQ ID NO:9; fragment shown in SEQ ID NO:23), and cardiac troponin I from human (Swiss Prot P19429; full length shown in SEQ ID NO:10; fragment shown in SEQ ID NO:24), rabbit (Swiss Prot P02646; full length shown in SEQ ID NO:11; fragment shown in SEQ ID NO:25), rat (Swiss Prot P23693; full length shown in SEQ ID NO:2; fragment shown in SEQ ID NO:16), chick Swiss Prot P27673; full length shown in SEQ ID NO:12; fragment shown in SEQ ID NO:26) and bovine (Swiss Prot PP08057; full length shown in SEQ ID NO:13; fragment shown in SEQ ID NO:27). Also shown is a comparison of amino acid sequences of the minimal inhibitory region and amino acids adjacent thereto for fast skeletal troponin I from chick (Swiss Prot P02644; full length shown in SEQ ID NO:3; fragment shown in the SEQ ID NO:30), mouse (Swiss Prot P13412; full length shown in SEQ ID NO:4; fragment shown in SEQ ID NO:31), human (Swiss Prot P48788; full length shown in SEQ ID NO:5; fragment shown in SEQ ID NO:32), rat (Swiss Prot P27768; full length shown in SEQ ID NO:1; fragment shown in SEQ ID NO:28) and rabbit (Swiss Prot P02643; full length shown in SEQ ID NO:6; fragment shown in SEQ ID NO:33), slow skeletal troponin I from human (Swiss Prot P19237; full length shown in SEQ ID NO:7; fragment shown in SEQ ID NO:34), rabbit (Swiss Prot P02645; full length shown in SEQ ID NO:9; fragment shown in SEQ ID NO:36) and rat(Swiss Prot P13413; full length shown in SEQ ID NO:8; fragment shown in SEQ ID NO:35) and, cardiac troponin I from human (Swiss Prot P19429; full length shown in SEQ ID NO:10; fragment shown in SEQ ID NO:37), mouse (Swiss Prot 48787; full length shown in SEQ ID NO:14, fragment shown in SEQ ID NO:40), rabbit (Swiss Prot P02646; full length shown in SEQ ID NO:11; fragment shown in SEQ ID NO:38), rat (Swiss Prot P23693; full length shown in SEQ ID NO:2; fragment shown in SEQ ID NO:29), and bovine (Swiss Prot P08057; full length shown in SEQ ID NO:13; fragment shown in SEQ ID NO:39).

DETAILED DESCRIPTION OF THE INVENTION

Figure 1:
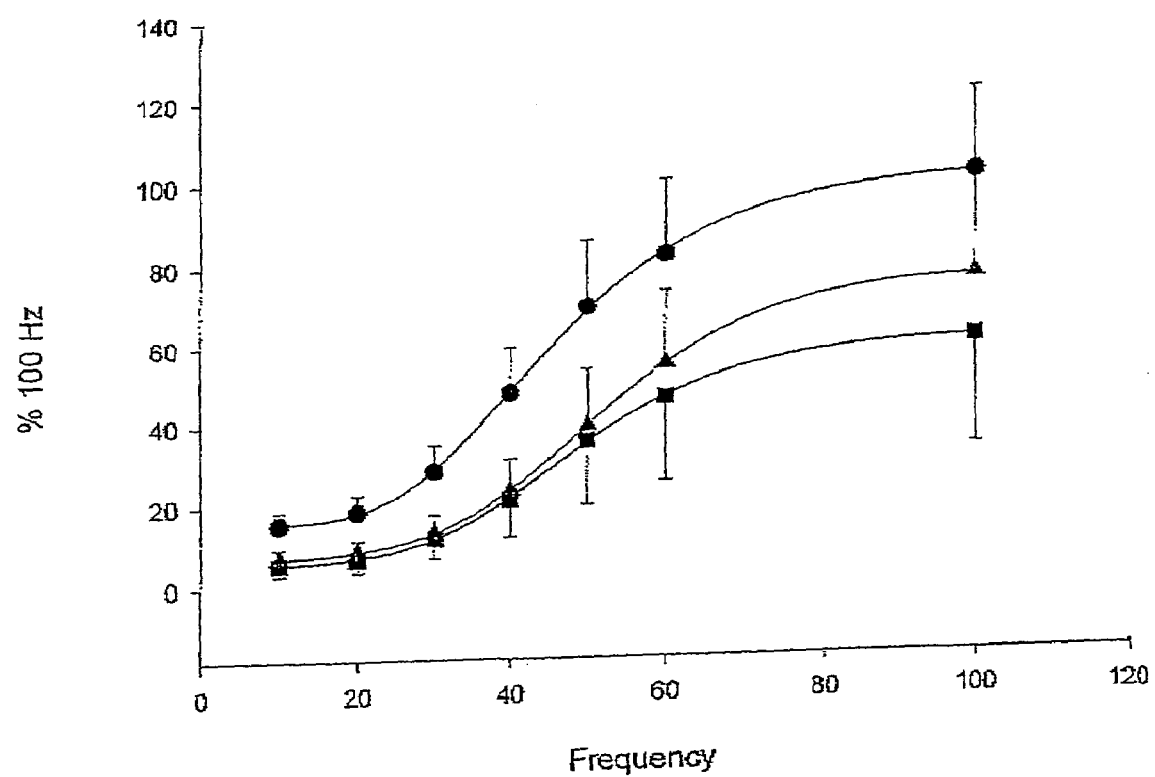
FIG. 1 provides a comparison of normalized force-frequency curves of the extensor digitorum longus (EDL) of rats obtained before (control, closed circle), immediately after 90 minutes of low flow ischemia (I/R EDL, closed square) and after 30 minutes reperfusion (closed triangle). Frequencies of 10, 20, 30, 40, 50, 60 and 100 Hz were applied to the sciatic nerve. Values (±SEM) were normalized to those at 100 Hz, control. Curves at 90 and 90+30 minutes did not differ but both differed significantly from control ($P<0.01$, repeated measures ANOVA at each frequency). Control curves for sham and I/R EDL were identical at all frequencies.

Using proteomics combined with physiological measurements, post-translationally modified myofilament proteins have now been identified which are associated with altered contractile function of muscles. In particular, new monophosphorylated and/or diphosphorylated forms of troponin I phosphorylated at the C terminus and/or adjacent to the minimal inhibitory region of troponin I have now been identified in skeletal and cardiac muscle. Further, as show herein, the phosphorylation state of troponin I is altered in injured muscle tissue as compared to control muscle tissue.

By "altered contractile function" as used herein it is meant either a decrease or increase in force of contraction and/or the economy of contraction and/or contractility and/or calcium sensitivity of a muscle fiber or myofibrils resulting from an alteration in the phosphorylation state of troponin I in a subject.

Unless otherwise specified herein, when using the term troponin I, it is meant to be inclusive of all isoforms of troponin I (e.g., cardiac troponin I, fast skeletal troponin I and slow skeletal troponin I).

Further, when using the phrase "phosphorylated troponin I" it is meant a troponin I protein phosphorylated at a site in the C terminus and/or adjacent to the minimal inhibitory region of troponin I. Accordingly, by monophosphorylated troponin I, it is meant a troponin I protein phosphorylated at either a site in the C terminus or a site adjacent to the minimal inhibitory region of troponin I. By diphosphorylated troponin I, it is meant a troponin I protein phosphorylated at sites in the C terminus and adjacent to the minimal inhibitory region of troponin I.

As used herein, by the phrase "phosphorylation state of troponin I" it is meant to be inclusive of the determination of a level or amount of a phosphorylated troponin I protein or isoform of troponin I protein or a ratio or protein profile of phosphorylated versus native troponin I protein or isoforms thereof, a ratio or protein profile of phosphorylated troponin I or an isoform thereof versus other modifications of troponin I, and a ratio or protein profile of phosphorylated troponin I or an isoform thereof versus other modified or unmodified myofilament proteins. For example, by phosphorylation state it is meant to include, but is not limited to, determination of a level of a monophosphorylated troponin I protein, a level of diphosphorylated troponin I protein, a level of total (meaning both mono-and di-) phosphorylated troponin I protein, a level of a monophosphorylated isoform of troponin I, a level of a diphosphorylated isoform of troponin I, a level of total (meaning both mono-and di-) phosphorylated isoform of troponin I, a ratio of native troponin I protein compared to a monophosphorylated troponin I protein, a ratio of native troponin I protein compared to diphosphorylated troponin I protein, a ratio of native troponin I protein compared to total (meaning both mono- and di-) phosphorylated troponin I protein, a ratio of a monophosphorylated troponin I protein compared to diphosphorylated troponin I protein, a ratio of a native isoform of troponin I protein compared to the monophosphorylated isoform of troponin I protein, a ratio of a native isoform of troponin I protein compared to the diphosphorylated isoform of troponin I protein, a ratio of a native isoform of troponin I protein compared to total (meaning both mono-and di-) phosphorylated isoform of troponin I protein, a ratio of a monophosphorylated isoform of troponin I protein compared to a diphosphorylated isoform troponin I protein, a ratio of total phosphorylated troponin I (meaning both mono-and di-) compared to one or more different modified troponin I proteins, a ratio of a monophosphorylated troponin I compared to one or more different modified troponin I proteins, a ratio of a diphosphorylated troponin I compared to one or more different modified troponin I proteins, a ratio of total (meaning both mono- and di-) phosphorylated isoform of troponin I protein compared to one or more different modified forms of that isoform of troponin I protein, a ratio of a monophosphorylated isoform of troponin I protein compared to one or more different modified forms of that isoform of troponin I protein, a ratio of a diphosphorylated isoform of troponin I protein compared to one or more different modified forms of that isoform of troponin I protein, a ratio of total phosphorylated troponin I (meaning both mono-and di-) compared to a different modified or unmodified myofilament protein or proteins, a ratio of a monophosphorylated troponin I compared to a different modified or unmodified myofilament protein or proteins, a ratio of a diphosphorylated troponin I compared to a different modified or unmodified myofilament protein or proteins, a ratio of total (meaning both mono-and di-) phosphorylated isoform of troponin I protein compared to a different modified or unmodified myofilament protein or proteins, a ratio of a monophosphorylated isoform of troponin I protein compared to a different modified or unmodified myofilament protein or proteins, and a ratio of a diphosphorylated isoform of troponin I protein compared to a different modified or unmodified myofilament protein or proteins. The phosphorylation state of troponin I may be determined at a single time point in a single sample obtained from a subject or may be monitored in a subject for alterations from several samples obtained over a selected period of time.

By "altered" or "alteration" with respect to phosphorylation state, it is meant a change such as an increase or decrease in the level or a difference in ratios as set forth above of a phosphorylated troponin I protein or proteins in the biological sample as compared to a control.

By "control" it is meant, a sample obtained from an individual known not to have muscle tissue injury, a sample obtained from the same subject, also referred to herein as a first sample or first biological sample, or a standard from data obtained from a data bank corresponding to a currently accepted normal phosphorylation state of troponin I or a phosphorylation state correlated with a known level of muscle tissue injury. The comparison between the control and a sample obtained from a subject, sometimes referred to herein as the second sample, performed may be a straightforward comparison, such as a ratio, or it may involve weighting of one or more of the measures relative to, for example, their importance to the particular situation under consideration. The comparison may also involve subjecting the measurement data to any appropriate statistical analysis.

By the phrase "injured muscle tissue", as used herein, it is meant to be inclusive of any damage and/or dysfunction of muscle cells and/or tissue resulting from insults including, but not limited to, stress, hypoxia, hyperoxia hypoxemia, infection, toxins, drugs (e.g. chemotherapeutics with muscle damaging side effects as well as drugs of abuse such as cocaine and alcohol), hypertension, ischemia (inclusive of conditions wherein blood flow is completely occluded as well as conditions wherein blood flow is decreased as compared to normal flow), ischemia reperfusion, hyperperfusion, hypoperfusion, exercise damage, blunt trauma, heart transplantation and/or rejection, inflammation, and pressure damage such as that caused by atmospheric pressure changes. By injured muscle tissue, it is also meant the damage and/or dysfunction occurring in diseases such as rhabdomyolysis, muscular dystrophy, sepsis, septicemia, respiratory diseases including, but not restricted to, chronic obstructive pulmonary disease, emphysema, asthma and bronchitis, bullectomy (lung reduction surgery), ventilation weaning, and following insult due to surgery or other trauma. By injured muscle tissue it is also meant to be inclusive of the damage or dysfunction from any insult or stress that activates or is associated with activation of a protease and/or a cross-linking enzyme such that modification (e.g., cross-linking, degradation) of cardiac myofilament proteins occurs. The injury to the muscle tissue may be acute, where it can result from any brief (acute) ischemic/hypoxic period (e.g., 30 seconds to 2 days) such as stunning, or pre-conditioning such as infarction (e.g., myocardial infarction (MI)), unstable angina and the like. In some cases, such as in stunning, acute muscle injury may be reversible. Muscle injury may also be chronic, where it can result from longer (chronic) ischemic/hypoxic episodes (e.g., durations of days to years), such as heart failure (HF) and diabetes. Chronic muscle injury includes situations where muscle injury (e.g., due to necrosis or apoptosis and loss of cell membrane integrity) causes the muscle to have to compensate for a reduction and/or loss in muscle cells and/or function. This leads to hypertrophy or atrophy of the muscle. Under these conditions, the phosphorylation state of troponin I may be altered in a time dependent manner. Further, as will be understood by those of skill in the art upon reading this disclosure, the phosphorylation state of troponin I is dynamic and provides valuable prognostic information in both acute and chronic muscle injury.

In accordance with the invention, the phosphorylation state of troponin I in a biological sample is determined. The biological sample can be obtained from any subject exhibiting, exposed to, suspected of having, or being treated for, a condition or conditions which could cause injured muscle tissue. For diagnostic and monitoring purposes, the phosphorylation state of troponin I can be assessed in a single sample obtained from a subject. In a preferred embodiment, however, injured muscle tissue is diagnosed or monitored in a subject by obtaining at least two biological samples from a subject at different times (i.e., not simultaneously), and evaluating the samples for a change with time in the phosphorylation state of troponin I.

The phosphorylation state of the troponin proteins identified herein is therefore applicable to diagnosis and/or monitoring of any disease, disorder or condition of cardiac muscle and/or skeletal muscle wherein the muscle tissue is injured. Further, determination of the phosphorylation state in accordance with the present invention is applicable to acute as well as chronic muscle injury. Moreover, the methods of the invention can be used to diagnose not only whether a subject has experienced muscle injury, but also whether that injury is acute or chronic. This is achieved in the invention by providing for the detection and characterization of the phosphorylation state of troponin I, and associating specific or unique states of phosphorylation with either acute or chronic muscle injury. For example, a biological sample containing protein-protein complexes involving cardiac troponin I of which only a small proportion (e.g., less than 10%) are phosphorylated may indicate acute muscle damage, such as that resulting from MI or unstable angina. If, however, analysis of a biological sample revealed a much greater proportion (e.g., about 50%) of such phosphorylated troponin I complexes, this may indicate chronic muscle damage such as that resulting from HF.

Chronic injury to the heart will cause remodelling and hypertrophy, with loss of cells via necrosis or apoptosis therefore allowing monitoring by serum samples and when possible tissue samples (at time of heart surgery if appropriate). Accordingly, the phosphorylation state of troponin I can also be determined in a biological sample such as blood and the presence or quantity or quality of phosphorylated troponin I is indicative of the stage of disease.

The invention is also applicable to monitoring of the rehabilitation of patients with muscle damage, disease such as rhabdomyolysis, respiratory diseases such as, but not restricted to, chronic obstructive pulmonary disease, emphysema, asthma and bronchitis, bullectomy (lung reduction surgery), and following insult due to surgery or other trauma. The invention further provides for the assessment of the appropriateness of performance enhancing drugs and/or the level of training in athletes and animals such as race horses, where the phosphorylation state of troponin I can be monitored for detection of muscle injury.

The term "subject" as used herein is intended to include any mammal susceptible to muscle damage, particularly cardiac or skeletal muscle damage (e.g., horses, dogs, humans). In a preferred embodiment, the subject is a primate. In an even more preferred embodiment, the primate is a human.

The term "obtaining" is intended to include recovery of a biological sample from a subject in a way such that the post-translationally modified protein is retained in a form that can be recognized by an antibody specific for the post-translationally modified protein. Biological samples can be obtained from a subject using methods known in the art. For example, blood can be drawn from a subject or a biopsy tissue can be obtained from a subject undergoing surgery, using standard techniques. Examples of biological samples include muscle tissue samples and biological fluids including, but not limited to, blood, serum, plasma, lymph, urine, cerebrospinal fluid, amniotic fluid and any other bodily fluid containing troponin I.

Assessment of the phosphorylation state of troponin I in a biological sample can be performed by incubating the biological sample with a compound specific for a phosphorylated troponin I protein of the present invention, under conditions which allow the compound to form a complex with the phosphorylated troponin I protein, and then detecting the complex, for example, by assaying for the presence of a label attached to the compound. Alternatively, the phosphorylation state of troponin I can be assessed by comparison of binding of a compound specific for native troponin I and binding of a compound which binds to native as well as phosphorylated troponin I. Examples of such compounds include, but are not limited to antibodies, aptamers, and peptides or proteins specific for troponin I. Assay formats well known to those of skill in the art which can be routinely adapted to determination of the phosphorylation state of troponin I in a biological sample include, but are not limited to, ELISA, RIA analysis (immunological detection), and determination of peptides or proteins that bind to phosphorylated and/or native forms of troponin I.

Assessment of the phosphorylation state of troponin I in a biological sample can also be performed by direct detection of unmodified and/or post-translationally modified protein or proteins in the sample, using, for example, chromatography techniques such as HPLC [detection based on differences in retention time], electrophoresis or surface enhanced laser disorption ionization (i.e., SELDI) [detection based on mass differences] or by chemical detection or by manipulation of the post-translation modification directly wherein the modified proteins, if present, are dephosphorylated enzymatically.

Any of these analyses, alone or in combination, can be used to determine the phosphorylation state of troponin I in a biological sample. Further, the appearance and/or disappearance of phosphorylated troponin I or a phosphorylated isoform of troponin I can be used as indicators of muscle damage.

The phosphorylation state of troponin I is regulated by a balance between the activity of kinase(s) and phosphatase(s) responsible for phosphorylation and dephosphorylation, respectively, at these phosphorylation sites. Accordingly, the phosphorylation state of troponin I can be altered in muscle tissue via alteration of the level and/or activity of one or both of these enzymes. Thus, another aspect of the invention relates to compositions comprising an agent targeted to a phosphatase and/or kinase that can alter the phosphorylation state of troponin I and methods for modulating the phosphorylation state of troponin I using such compositions. As shown herein, the phosphatase protein phosphatase 1 (PP-I) is capable of dephosphorylating troponin I at phosphorylation sites identified at the C terminus and adjacent to the minimal inhibitory region while the kinase p21 activated kinase is capable of phosphorylating troponin I in at least one of these phosphorylation sites. Accordingly, in a preferred embodiment of this aspect of the present invention, the agent alters the level and/or activity of a phosphatase such as PP-I or a kinase such as p21-activated kinase. Such compositions and methods are useful in the treatment of muscle injury, and more particularly in altering the calcium sensitivity of muscle tissue and/or the force of contraction, the economy of contraction and/or contractility of muscle tissue in a subject.

Phosphorylated troponin I proteins of the present invention were isolated in fast skeletal troponin I. In these experiments, ischemic reperfusion was used to induce contractile dysfunction of the in situ extensor digitorum longus (EDL) of rats. FIG. 1 shows force-frequency curves obtained before (control), immediately after termination of reduced blood flow (low flow ischemia), and 30 minutes following reinstitution of perfusion (reperfusion) which was associated with a transient decrease in whole body mean arterial pressure consistent with reactive hyperaemia. These curves were used to assess whole muscle contractile status. Because the rat hindlimb contains numerous arterial collaterals, femoral artery ligation does not cause complete cessation of perfusion. Instead, it has been estimated that this procedure causes approximately a 33% reduction in blood flow. As shown in FIG. 1, however, this low flow ischemia for 90 minutes significantly depressed contractile function, even after 30 minutes of reperfusion. This depression in contractile function occurred without affecting half-relation time and time-to-peak tension (see Table 1).

TABLE 1

Comparison of twitch parameters of sham EDL (N = 11) and I/R EDL (n = 9) before (control), after 90 minutes of ischemia (for I/R EDL), and after 90 minutes of ischemia followed by 30 minutes of reperfusion (for I/R EDL)

| | ½relaxation time | | | time to peak tension | | |
|---|---|---|---|---|---|---|
| | Sham | I/R | p value | Sham | I/R | p value |
| Group | 0.043 ± 0.009 | 0.053 ± 0.015 | 0.215 | 0.015 ± 0.006 | 0.021 ± 0.008 | 0.568 |
| 90 min | 0.044 ± 0.009 | 0.041 ± 0.018 | 0.321 | 0.017 ± 0.003 | 0.016 ± 0.009 | 0.607 |
| 90 + 30 | 0.041 ± 0.011 | 0.040 ± 0.009 | 0.224 | 0.013 ± 0.011 | 0.013 ± 0.011 | 0.670 |

Figure 2:
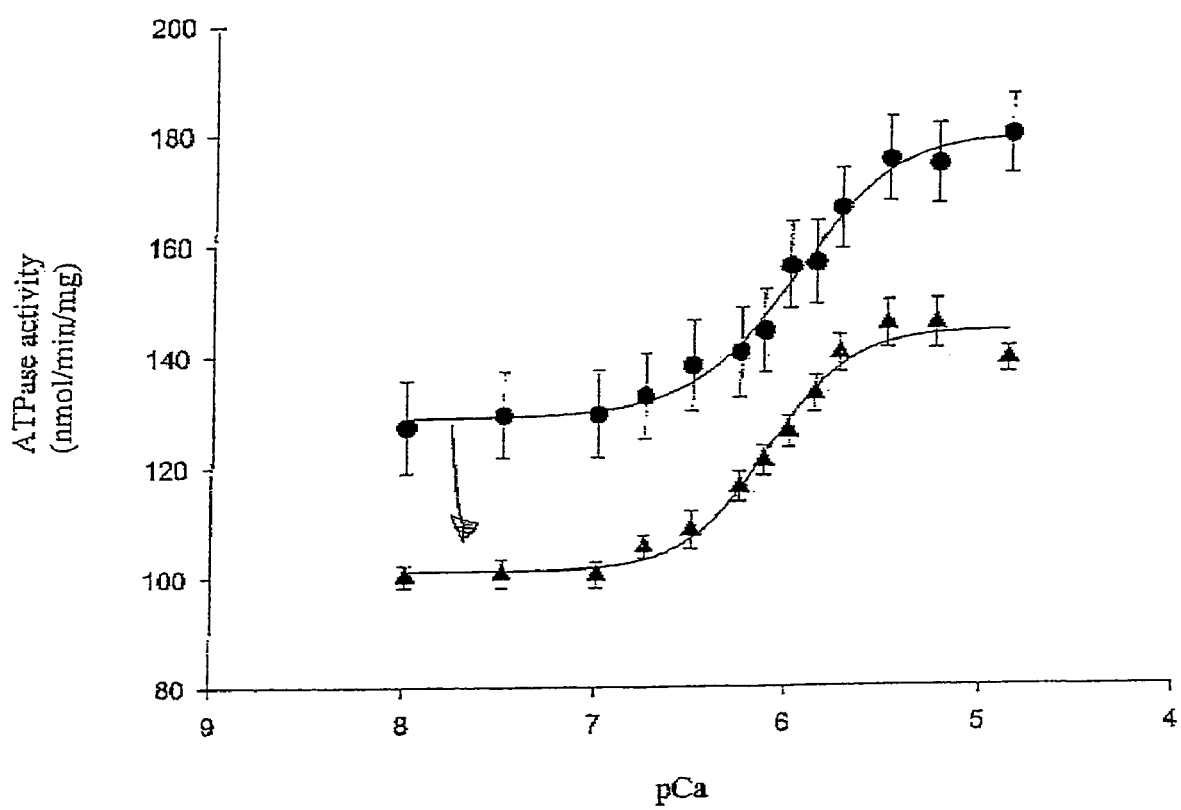
FIG. 2 shows the relationship of ATPase activity to pCa for myofibrils from sham (closed circle) and I/R EDL (closed triangle. The curve for I/R EDL myofibrils differs significantly from the sham (mean ±SEM, n=4, $p<0.05$, student's two-tailed t test).

To assess changes to the myofilament proteome associated with whole muscle dysfunction, myofibrils were isolated from the sham and I/R EDL muscle and ATPase activity was measured (see FIG. 2). I/R EDL displayed depressed $Ca^{2+}$-activated myofibril ATPase activity at all calcium concentrations compared to sham EDL ($P<0.05$), thus indicating a change in the regulation of contraction as a result of a modification to one or more myofilament proteins.

Figure 3A:
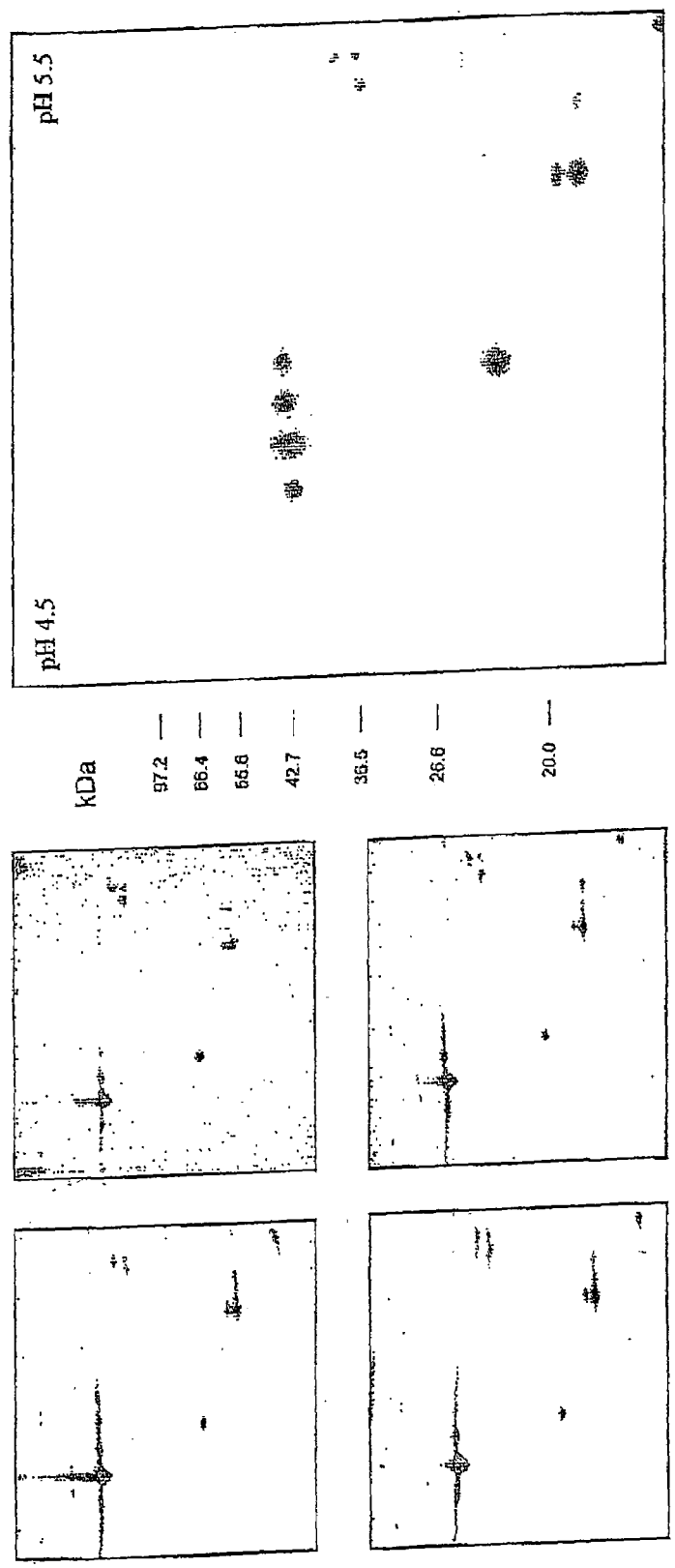
FIG. 3A provides four silver-stained 2-dimensional gels (pH 4.5–5.5) of I/R EDL myofibrils (left) and their computer generated composite (right). The positions of SDS-PAGE molecular weights standards are indicated on the left of the composite.
Figure 3B:
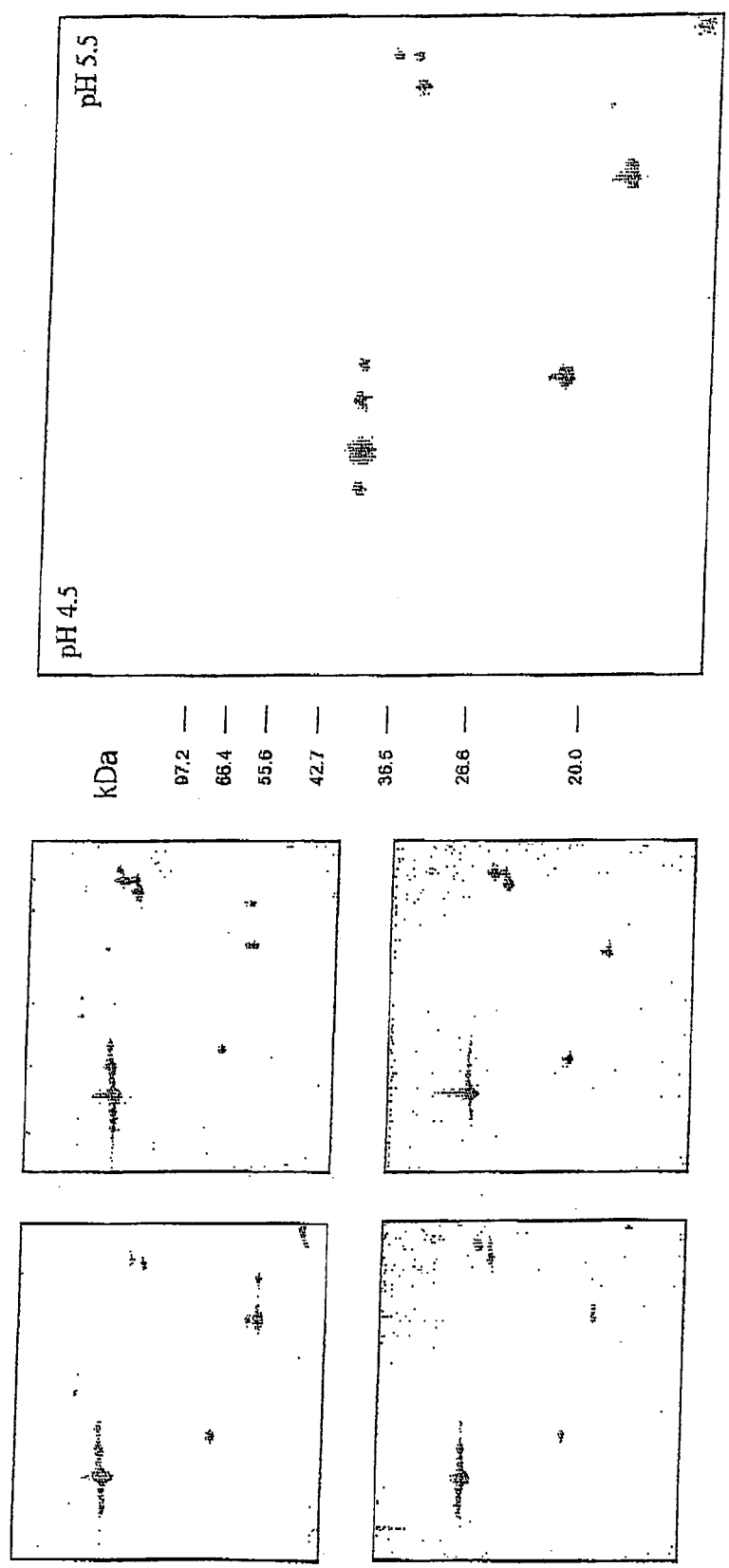
FIG. 3B provides four silver-stained 2-dimensional gels (pH 4.5–5.5) of sham EDL myofibrils (left) and their computer-generated composite (right). The positions of SDS-PAGE molecular weight standards are indicated on the left of the composite.

Post-translational modifications to the myofilament subproteome were then examined. No new forms or changes in quantity of the proteins actin, desmin, tropomyosin, troponin T and myosin light chain 1 were identified by 2-dimensional SDS-PAGE using a pH gradient of 4.5 to 5.5 (see FIGS. 3A and B).

Figure 4:
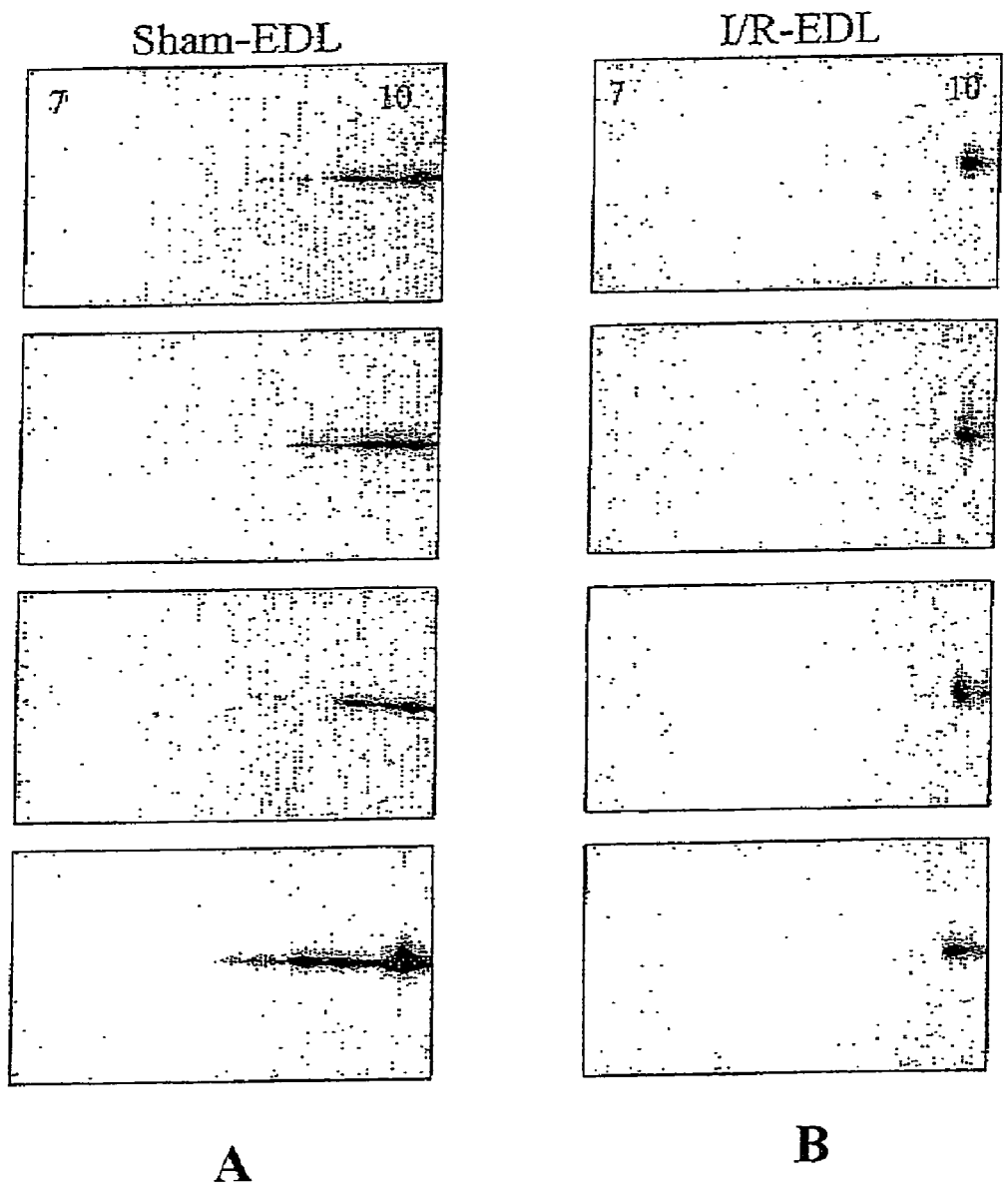
FIGS. 4A–B show western blots of 2-dimensional gels from sham (FIG. 4A) and I/R EDL (FIG. 4B) for fast skeletal troponin I using mAb FI-32.

Post-translational modifications to fast skeletal troponin I were examined with an IPG pH 7–10 gradient using low protein concentrations followed by western blotting. FIG. 4 shows 2-dimensional western blots for fast skeletal troponin I probed with the monoclonal antibody FI-32 in myofibrils of sham (FIG. 4A) and I/R EDL (FIG. 4B) animals. In myofibrils of sham EDL, fast skeletal troponin I presented as three protein spots, the native or unmodified form and two spots resolving at a more acidic pI which represent post-translationally modified forms, referred to herein as α or monophosphorylated and β or diphosphorylated forms of the protein. Upon prolonged exposure, myofibrils of I/R EDL probed with the same monoclonal antibody also revealed the same three spots thus indicating a decreased extent of phosphorylation in injured muscle tissue.

To ascertain further differences between sham and I/R EDL myofibrils, western blots for fast skeletal troponin I from sham and I/R EDL myofibrils were scanned and digitized to obtain computer-generated volume charts. These 3-dimensional representations of density of exposure allowed for selection of equally developed exposures within the linear range of the film, thereby allowing comparison of the fast skeletal troponin I signals between sham and I/R EDL myofibrils. Signals within 10% of the upper limit of the linear range of the film reliably revealed modified forms of fast skeletal troponin I in myofibrils of sham EDL.

Figure 5:
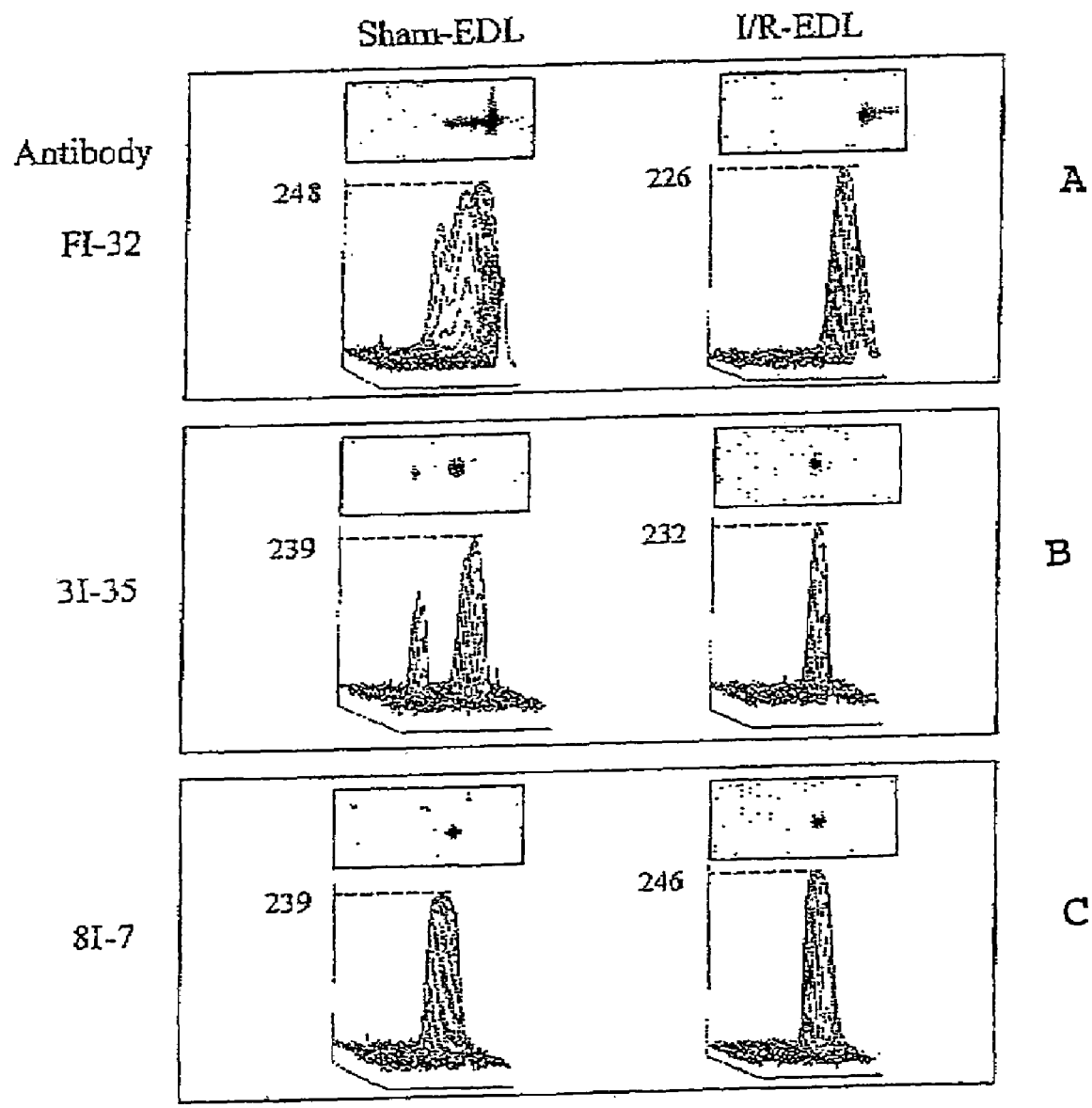
FIGS. 5A–C shows enlargements of 2-dimensional western blots of sham and I/R EDL myofibrils probed for fast skeletal troponin I using 3 different monoclonal antibodies, FI-32 (FIG. 5A), 3I-35 (FIG. 5B) and 8I-7 (FIG. 5C).
Figure 6:
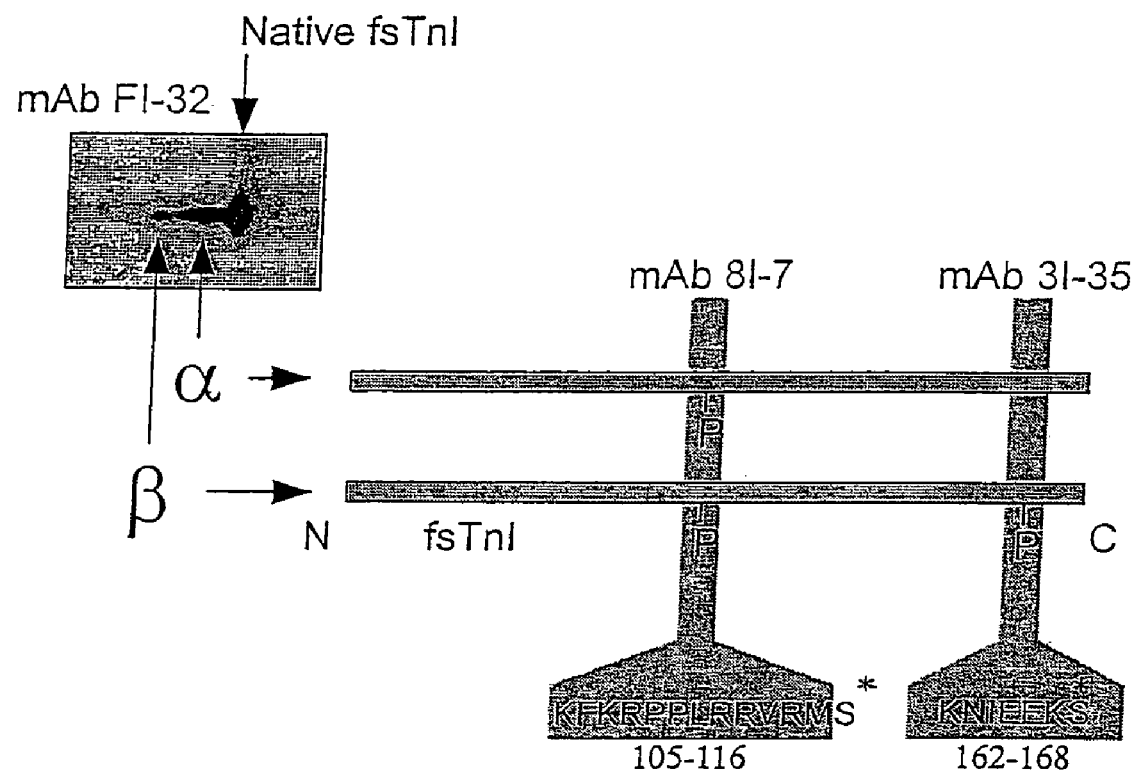
FIG. 6 shows a schematic of the α or monophosphorylated (top) and β or diphosphorylated (bottom) forms of fast skeletal troponin I. The epitopes of two monoclonal antibodies, mAb 8I-7 and mAb 3I-35, as shown as shaded regions with the phosphorylatable serine residues identified (*). Phosphorylation of serine 117 and serine 168 affects the affinities of mAb 8I-7 and 3I-35, respectively.

Post-translational modifications can alter the binding affinity of a monoclonal antibody for the antigen when located within or near the epitope. Accordingly, the abilities of different antibodies to detect various forms of fast skeletal troponin I in sham EDL myofibrils were used to identify regions of fast skeletal troponin I containing the post-translational modifications. Monoclonal antibodies against troponin I used in these experiments included mAb FI-32, mAb 8I-7 and mAb 3I-35. As shown in FIG. 5, not all of these monoclonal antibodies detected the various phosphorylated forms of fast skeletal troponin I. For example, all three mAbs detected the native form of fast skeletal troponin I but mAb 3I-35 did not detect the diphosphorylated β form (see FIG. 5B) and mAb 8I-7 detected neither the monophosphorylated α form or the diphosphorylated β form (see FIG. 5C). Prolonged exposure with either mAb 3I-35 or 8I-7 did not reveal the additional forms. These results indicate that each of the post-translational modifications, which resulted in the formation of the α and β forms of fast skeletal troponin I occurred within, or in very close proximity to the epitopes of mAb 3I-35 and 8I-7, thus affecting their affinities. See FIG. 6. The epitope of mAb 3I-35 corresponds to amino acids 162–168 of the C terminus of rat fast skeletal troponin I and the epitope of mAb 8I-7 corresponds to amino acids 105–116 of the inhibitory region of rat fast skeletal troponin I (numbering of amino acids of rat fast skeletal protein corresponds to that set forth in the amino acid sequence of Swiss Prot P27768 (SEQ ID NO:1)). Accordingly, these results indicate that the α and β forms of fast skeletal troponin I are associated with post-translational modifications occurring within or near the amino acid sequences 105–116 and 162–168 of SEQ ID NO:1.

To characterize the nature of the post-translational modification, the myofibrils were dephosphorylated prior to 2-dimensional SDS-PAGE to determine if the α and β forms resulted from phosphorylation of fast skeletal troponin I. Neither form was evident in samples after dephosphorylation with PP-I, indicating that the post-translational modifications were indeed phosphorylation. Examination of the amino acid sequences of the epitopes of mabs 8I-7 and 3T-35 revealed serines at amino acid position 117 adjacent to the minimal inhibitory region of rat skeletal troponin I and position 168 at the C terminus.

Further evidence of phosphorylation of fast skeletal troponin I at these sites was obtained in experiments with alkaline phosphatase. Dephosphorylation experiments with alkaline phosphatase were unsuccessful. However, alkaline phosphatase cannot dephosphorylate serine and threonine residues adjacent to basic amino acids. Serine 117 and serine 168 of rat fast skeletal troponin I are both adjacent to basic residues.

Figure 7:
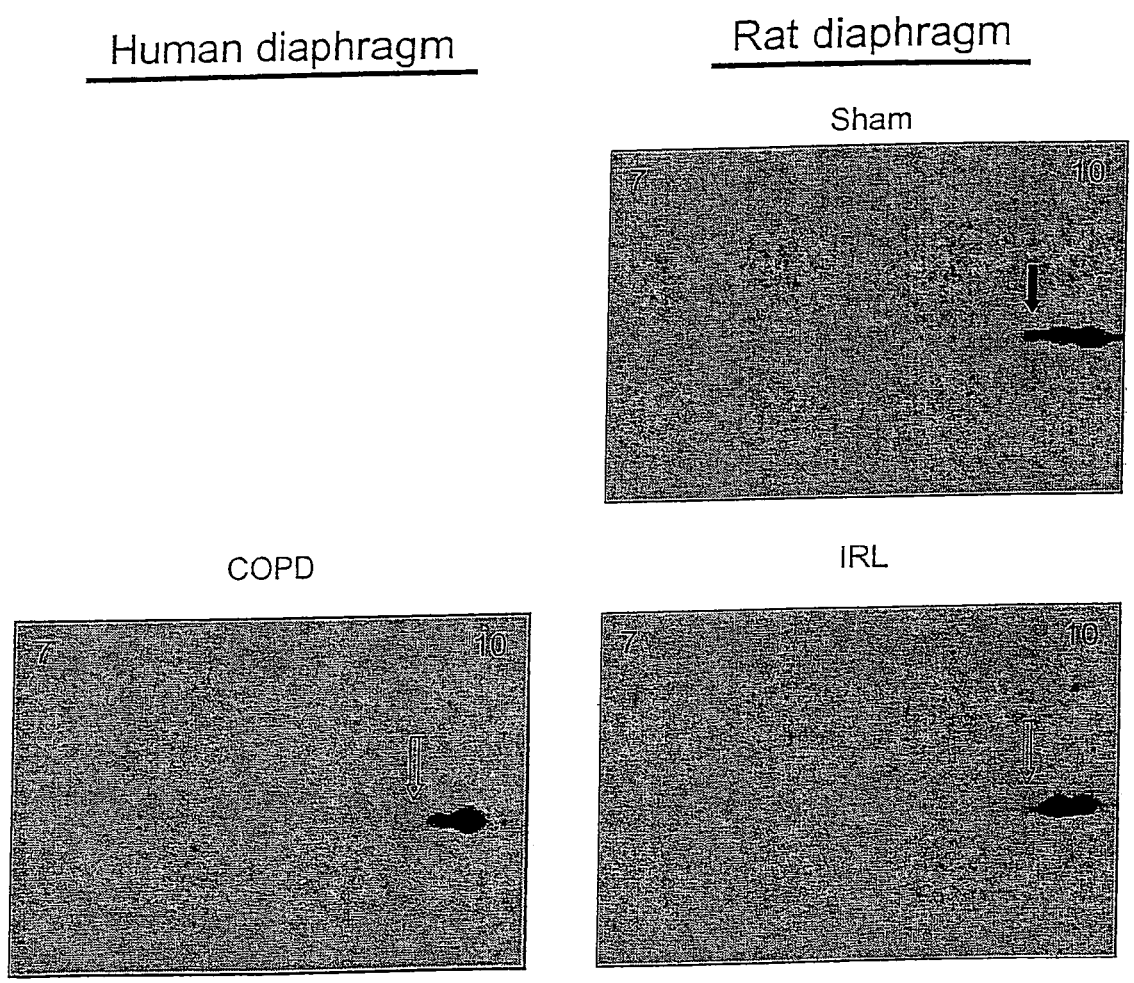
FIG. 7 shows western blots comparing post-translationally modified fast skeletal troponin I in human diaphragm tissue obtained from a patient with severe chronic obstructive pulmonary disease, rat diaphragm tissue from an anesthetized, spontaneously breathing rat breathing an inspiratory load (IRL) until failure resulting from diaphragmatic fatigue (as opposed to central fatigue), and rat diaphragm from a sham (control) rat.

Proteomic analysis was also performed on diaphragmatic tissue from an in vivo rat model of diaphragmatic fatigue and compared with diaphragmatic tissue from a control or sham rat. As shown in FIG. 7, diaphragm of the sham rat contains the native form of fast skeletal troponin I and two acid-shifted spots believed to be the α and β phosphorylated forms of fast skeletal troponin I. In the inspiratory resistive loaded (IRL) rat, the most acidic spot is absent. Thus, like the I/R EDL rats, the extent of phosphorylation of fast skeletal troponin I is decreased in muscle injury. Proteomic analysis of diaphragmatic tissue from a human patient with severe chronic obstructive pulmonary disease undergoing lung volume reduction surgery by western blot showed a similar pattern to that of the IRL rat wherein only one acidic-shifted spot was detected. Accordingly, it appears that the extent of phosphorylation of human fast skeletal troponin I is also decreased upon muscle injury.

Phosphorylation sites at the C terminus and adjacent to the minimal inhibitory region of cardiac troponin I have also been identified and a monophosphorylated form of cardiac troponin I phosphorylated adjacent to the minimal inhibitory region of the protein has been isolated. Specifically, a rat cardiac troponin I phosphorylated at serine 149 of Swiss Prot P23693 (SEQ ID NO:2) was isolated. Further, phosphorylation at this site is associated with p21-activated kinase-induced calcium sensitization of cardiac muscle contraction. Thus, the extent of phosphorylation of cardiac troponin I is also associated with altered contractile function of muscle tissue. In cardiac muscle, an increase in phosphorylated troponin I is also associated with increased contractile function due to increased calcium sensitivity.

The identified phosphorylation sites in the C terminus and adjacent to the minimal inhibitory region of fast skeletal and cardiac troponin I of the rat troponin I isoforms were compared to various mammalian species. As shown in FIG. 8, the serines in these regions are conserved in all mammalian troponin I isoforms examined.

Accordingly, one aspect of the present invention relates to isolated phosphorylated mammalian troponin I proteins. In a preferred embodiment the isolated proteins comprise a troponin I phosphorylated at its C terminus and/or phosphorylated adjacent to its minimal inhibitory region. By "adjacent" it is meant phosphorylation within 5, or more preferably 2 amino acids of the minimal inhibitory region. For human and rat fast skeletal troponin I, phosphorylation sites are present at serine 117 and serine 168. For human cardiac troponin I, phosphorylation sites are present at serine 149 and serine 198. For rat cardiac troponin I, phosphorylation sites are present at serine 150 and serine 199. For human and rat slow skeletal troponin I, phosphorylation sites are present at serine 118 and serine 168.

The present invention also provides methods and kits containing antibodies or aptamers capable of distinguishing between native troponin I and these phosphorylated forms of troponin I. As shown herein, various commercially available antibodies against native troponin I exhibit varying specificities toward the newly discovered phosphorylated forms of troponin I disclosed herein. For example, polyclonal antibodies and the monoclonal antibody mAb FI-32 can be used to detect native as well as the α and β phosphorylated forms of fast skeletal troponin I. mAb FI-32 and mAb 3I-35 can be used to detect native and the α monophosphorylated form of troponin I. mAb 8I-7 can be used to selectively detect native troponin I.

Accordingly, in one embodiment of the present invention, methods and kits are provided for detecting both native troponin I and phosphorylated troponin I in a sample. In this embodiment, the sample is contacted with either a polyclonal antibody or a monoclonal antibody such as mAb FI-32 or an aptamer which binds to native troponin I and phosphorylated forms of troponin I. Kits for this embodiment comprise a polyclonal or monoclonal antibody or an aptamer which is capable of binding to both native troponin I and phosphorylated forms of troponin I.

In another embodiment of the present invention, methods and kits are provided which can distinguish native troponin I from a phosphorylated troponin I in a sample. In this embodiment, the sample is contacted with a monoclonal antibody such as mAb 8I-7 or an aptamer which binds to native troponin I but not to a phosphorylated troponin I. The sample can then be contacted with an antibody or aptamer which binds selectively to phosphorylated troponin I or to native and phosphorylated troponin I such as mAb FI-32. Accordingly, by contacting a sample with different combinations of these antibodies, native troponin I and the $\alpha$ and $\beta$ phosphorylated forms of the protein can be distinguished.

As will be understood by those of skill in the art upon reading this disclosure, additional antibodies to those exemplified herein can be used in the methods and kits of the present invention.

Further, the term "antibody" as used herein encompasses all forms of antibodies known in the art, such as polyclonal, monoclonal, chimeric, recombinatorial, single chain and humanized antibodies, as well as functional fragments thereof (e.g., F(ab')$_2$ fragments), either synthetic or native, labelled or unlabelled, which specifically bind to native and/or phosphorylated troponin I and/or selected isoforms of troponin I.

Monoclonal antibodies capable of recognizing phosphorylated troponin I proteins of the present invention can be prepared using methods well known in the art. Such methods are described, for example, in detail in U.S. Pat. No. 4,942,131 to Yamasaki et al., issued Jul. 17, 1990, and U.S. Pat. No. 5,583,053 to Kim, issued Dec. 10, 1996. The term "monoclonal antibody," as used herein, refers to a population of antibody molecules that contain only one species of an antigen binding site capable of immunoreacting with a particular epitope of troponin I. Said epitope may also be present in native myofilament protein. A monoclonal antibody composition thus typically displays a single binding affinity for a troponin I protein.

Monoclonal antibodies useful in the methods of the invention are directed to an epitope of troponin I, such that the complex formed between the antibody and troponin I can be recognized in detection assays such as ELISA, RIA etc. A monoclonal antibody to an epitope of troponin I can be prepared by using a technique which provides for the production of antibody molecules by continuous cell lines in culture. These include but are not limited to the hybridoma technique originally described by Kohler and Milstein (1975, *Nature* 256:495–497), and the more recent human B cell hybridoma technique (Kozbor et al. 1983, *Immunol Today* 4:72), EBV-hybridoma technique (Cole et al. 1985, *Monoclonal Antibodies and Cancer Therapy*, Alan R. Liss, Inc., pp. 77–96), and trioma techniques. Other methods which can effectively yield monoclonal antibodies useful in the present invention include phage display techniques (Marks et al. 1992, *J. Biol. Chem.* :16007–16010).

In one embodiment, the antibody preparation applied in the subject method is a monoclonal antibody produced by a hybridoma cell line. Hybridoma fusion techniques were first introduced by Kohler and Milstein (Kohler et al. 1975, *Nature* 256:495–97; Brown et al. 1981, *J. Immunol.* 127: 539–46; Brown et al. 1980, *J. Biol. Chem.* 255:4980–83; Yeh et al. 1976, *PNAS* 76:2927–31; and Yeh et al. 1982, *Int. J. Cancer* 29:269–75). Thus, the monoclonal antibody compositions of the present invention can be produced by immunizing an animal with a phosphorylated form of troponin I. The immunization is typically accomplished by administering the protein to an immunologically competent mammal in an immunologically effective amount, i.e., an amount sufficient to produce an immune response. Preferably, the mammal is a rabbit or a rodent such as a rat or a mouse. The mammal is then maintained for a period sufficient for the mammal to produce cells secreting antibody molecules that immunoreact with the post-translationally modified protein. Such immunoreaction is detected by screening the antibody molecules so produced for immunoreactivity with a preparation of the immunogen protein. Optionally, it may be desired to screen the antibody molecules with a preparation of the protein in the form in which it is to be detected by the antibody molecules in an assay. These screening methods are well known to those of skill in the art, e.g., ELISA, flow cytometry, and/or the Dipstick by Spectral Diagnostics Inc, Toronto, Canada.

A suspension of antibody-producing cells removed from each immunized mammal secreting the desired antibody is then prepared. After a sufficient time, the mouse is sacrificed and somatic antibody-producing lymphocytes are obtained. Antibody-producing cells may be derived from the lymph nodes, spleens and peripheral blood of primed animals. Spleen cells are preferred, and can be mechanically separated into individual cells in a physiologically tolerable medium using methods well known in the art. Mouse lymphocytes give a higher percentage of stable fusions with the mouse myelomas described below.

The spleen cell chromosomes encoding desired immunoglobulins are immortalized by fusing the spleen cells with myeloma cells, generally in the presence of a fusing agent such as polyethylene glycol (PEG). Any of a number of myeloma cell lines may be used as a fusion partner according to standard techniques; for example, the P3-NS1/1—Ag4-1, P3-x63-Ag8.653 or Sp2/O-Ag14 myeloma lines. These myeloma lines are available from the American Type Culture Collection (ATCC), Manassas, Va.

The resulting cells, which include the desired hybridomas, are then grown in a selective medium, such as HAT medium, in which non fused parental myeloma or lymphocyte cells eventually die. Only the hybridoma cells survive and can be grown under limiting dilution conditions to obtain isolated clones. The supernatants of the hybridomas are screened for the presence of antibody of the desired specificity, e.g., by immunoassay techniques using the antigen that has been used for immunization. Positive clones can then be subcloned under limiting dilution conditions and the monoclonal antibody produced can be isolated. Various conventional methods exist for isolation and purification of the monoclonal antibodies so as to free them from other proteins and other contaminants. Commonly used methods for purifying monoclonal antibodies include ammonium sulfate precipitation, ion exchange chromatography, and affinity chromatography (see, e.g., Zola et al. 1982, in: *Monoclonal Hybridoma Antibodies: Techniques And Applications*, Hurell (ed.), CRC Press, pp. 51–52). Hybridomas produced according to these methods can be propagated in vitro or in vivo (in ascites fluid) using techniques known in the art.

Monoclonal antibodies or fragments thereof suitable for use in the present invention (i.e., which recognize and specifically bind to native troponin I and/or phosphorylated forms of troponin I) can also be produced by other methods well known to those skilled in the art of recombinant DNA technology. Such alternative methods include the "combinatorial antibody display" method in which antibodies and antibody fragments having a particular antigen specificity are identified and isolated, and can be utilized to produce monoclonal anti-post-translationally modified protein antibodies (for descriptions of combinatorial antibody display see e.g., Sastry et al. 1989, *PNAS* 86:5728; Huse et al. 1989, *Science* 246:1275; and Orlandi et al. 1989, *PNAS* 86:3833). After immunizing an animal with an immunogen for the post-translationally modified protein as described above, the antibody repertoire of the resulting B-cell pool is cloned. Methods are generally known for directly obtaining the DNA sequence of the variable regions of a diverse population of immunoglobulin molecules by using a mixture of oligomer primers and PCR. For instance, mixed oligonucleotide primers corresponding to the 5' leader (signal peptide) sequences and/or framework 1 (FR1) sequences, as well as primers corresponding to a conserved 3' constant region primer can be used for PCR amplification of the heavy and light chain variable regions from a number of murine antibodies (Larrick et al. 1991, *Biotechniques* 11:152–156). A similar strategy can also been used to amplify human heavy and light chain variable regions from human antibodies (Larrick et al. 1991, *Methods: Companion to Methods in Enzymology* 2:106–110).

The V-gene library cloned from the immunization-derived antibody repertoire can be expressed by a population of display packages, preferably derived from filamentous phage, to form an antibody display library. Ideally, the display package comprises a system that allows the sampling of very large variegated antibody display libraries, rapid sorting after each affinity separation round, and easy isolation of the antibody gene from purified display packages. In addition to commercially available kits for generating phage display libraries (e.g., the *Pharmacia Recombinant Phage Antibody System*, catalog no. 27–9400–01; and the Stratagene SurfZAP™ phage display kit, catalog no. 240612), examples of methods and reagents particularly amenable for use in generating a variegated anti-post-translationally modified protein product antibody display library can be found in, for example, Ladner et al., U.S. Pat. No. 5,223,409; Kang et al., International Publication No. WO 92/18619; Dower et al., International Publication No. WO 91/17271; Winter et al., International Publication WO 92/20791; Markland et al., International Publication No. WO 92/15679; Breitling et al., International Publication WO 93/01288; McCafferty et al., International Publication No. WO 92/01047; Garrard et al., International Publication No. WO 92/09690; Ladner et al., International Publication No. WO 90/02809; Fuchs et al. 1991, *Bio/Technology* 9:1370–1372; Hay et al. 1992, *Hum Antibod Hybridomas* 3:81–85; Huse et al. 1989, *Science* 246:1275–1281; Griffiths et al. 1993, *EMBO J* 12:725–734; Hawkins et al. 1992, *J Mol Biol* 226:889–896; Clackson et al. 1991, *Nature* 352:624–628; Gram et al. 1992, *PNAS* 89:3576–3580; Garrad et al. 1991, *Bio/Technology* 9:1373–1377; Hoogenboom et al. 1991, *Nuc Acid Res* 19:4133–4137; and Barbas et al. 1991, *PNAS* 88:7978–7982.

The kits of the present invention may also comprise as a standard a phosphorylated troponin I protein. In a preferred embodiment, the standard comprises an α or β phosphorylated form of troponin I. Most preferred is a kit containing both the α or β phosphorylated forms troponin I as two separate standard. In a preferred embodiment, the antibody or antibodies and/or standard or standards are labelled and the kit further includes a reagent(s) appropriate for detecting the label.

As used herein the language "label" is intended to include any observable or measurable moiety which can be directly or indirectly attached to a complex formed between the antibody and the protein or standard so that the complex can be detected.

For example, the label can be a direct label which, in its natural state, is readily visible, either to the naked eye, or with the aid of an optical filter and/or applied stimulation, e.g. U.V. light to promote fluorescence. Examples of coloured labels, which can be used according to the present invention, include metallic sol particles, for example, gold sol particles such as those described by Leuvering (U.S. Pat. No. 4,313,734; dye sol particles such as described by Gribnau et al. (U.S. Pat. No. 4,373,932) and May et al. (WO 88/08534); dyed latex such as described by May, supra, Snyder (EP-A ) 280 559 and 0 281 327); or dyes encapsulated in liposomes as described in Campbell et al. (U.S. Pat. No. 4,703,017). Other direct labels include a radionucleotide, a fluorescent moiety or a luminescent moiety. In addition to these direct labelling devices, indirect labels including enzymes can also be used according to the present invention. Various types of enzyme linked immunoassays are well known in the art, for example, alkaline phosphatase, horseradish peroxidase, luciferase, beta-galactosidase, lysozyme, glucose-6-phosphate dehydrogenase, lactate dehydrogenase, and urease. These immunoassays and others have been discussed in Engvall et al. 1980, Enzyme Immunoassay ELISA and EMIT, *Methods in Enzymology*, 70:419–439 and in U.S. Pat. No. 4,857,453.

As will be understood by those of skill in the art upon reading this disclosure, the assays and kits described above can be adapted routinely by those of skill in the art to utilize aptamers rather than antibodies. Aptamers are single-stranded DNA molecules that, like antibodies, can bind target molecules with extraordinary affinity and specificity. Aptamers are available commercially through vendors such as SomaLogic (Boulder, Colo.).

Such kits and methods are useful in monitoring alterations in the phosphorylation state of troponin I which occurs in muscle damage.

The invention is further illustrated by the following examples, which should not be construed as further limiting. The contents of all references, pending patent applications, and published patents cited throughout this application are hereby expressly incorporated by reference.

EXAMPLES

Example 1

Surgical Preparation

Male Sprague-Dawley rats (200–250 grams) were randomly assigned to either a sham (sham-EDL) or low flow ischemia/reperfusion (I/R EDL) group. Rats were anesthetized with an intraperitoneal injection of pentobarbital sodium (35 mg/kg), supplemented (10% of the initial dose) when the animals displayed a brisk response to noxious stimulation of a tow pad. The EDL was prepared as described by Nishio and Jeejeebhoy (1991 J. Appl. Physiol. 88:753–760). In this procedure, in one hind limb, the sciatic nerve was prepared for stimulation, the femoral artery was exposed and the tendon of the EDL was separated from other tendons in the foot and cut. The upper femur, cleared of surrounding tissue, was secured in a clamp and the tendon was attached via a ligature and wire to a force transducer held in a micromanipulator. All exposed tissues of the leg, except for the EDL, were covered with VASELINE and plastic film to prevent desiccation and to maintain temperature. The exposed EDL was kept moist with a constant drip of warmed, 38° C. Ringer's solution. After determining the electrical threshold (T) for eliciting a twitch, the optimal length of the EDL was then determined using single supramaximal (10×T) shocks.

Example 2

Protocol

After the optimal muscle length was determined, the limb was allowed to equilibrate for 15 minutes. Blood flow was reduced by clamping only the femoral artery for 90 minutes. Force frequency curve (330 ms trains at 10, 20, 30, 40, 50, 60 and 100 Hz) were obtained before, immediately after termination of low flow ischemia, and 30 minutes following reperfusion (recovery). The EDL was harvested and immediately used for the preparation of skeletal myofibrils.

Example 3

Purification of Myofibrils

Skeletal myofibrils were isolated from rat EDL tissue at 4° C. as described by Pagani and Solaro (1984 *Am. J. Physiol.* 247:H909–H915). All solutions used were in the purification of the myofibrils and the ATPase assay contained a protease inhibitor cocktail (100 µM phenylmethylsulfonyl fluoride, 6 µM leupeptide, 5 µM pepstatin A, and 1 µM aprotinin) and were prepared with HPLC grade water. The EDL was homogenized in K60 (1 M imidazole (pH 7.0), 1 M KCl and 2.5 M $MgCl_2$)+0.1 M EGTA, followed by centrifugation (12,000 g) for 10 minutes. The pellet was resuspended in K60+1% (v/v) Triton X-100, equilibrated for 10 minutes, then centrifuged (15,000 g for 10 minutes). The pellet was resuspended in K60 buffer and centrifuged (12,000 g). This was repeated three times to remove all traces of Triton. The freshly prepared myofibrils were divided into three aliquots for 1) the myofibril ATPase assay, 2) protein concentration measurements using the Lowry method, and 3) stored at −70° C. for subsequent two-dimensional gel electrophoresis.

Example 4

Myofibril ATPase Assay

All assays were completed within 6 hours of the tissue harvest. $Ca^{2+}$-dependent $Mg^{2+}$ATPase activity of isolated myofibrils was carried out in a 100 µl reaction mixture containing 70 µl myofibrils (0.3–0.5 mg/ml myofibrillar protein in 1 M imidazole, pH 7.0), 1 M KCl and 7.5 M $MgCl_2$) and 10 µl calcium solutions ([$Ca^{2+}$] varied from pCa 8 to 4.875). The reaction mixture was pre-incubated at 30° C. for 5 minutes and the reaction was initiated by adding 20 µl of 7 mM $Na_2ATP$. The reaction was terminated after 10 minutes. Inorganic phosphate release was determined using the methods of Carter and Karl (1982 J. Biochem. Biophys. Methods 7:7–13). Less than 10% of the ATP was hydrolyzed over the course of the reaction. The phosphate content of the blank control (without ATP) was subtracted from each value and compare to a standard phosphate curve.

Example 5

Two-dimensional Gel Electrophoresis (2-DE)

Myofibrils were homogenized in 2% SDS, 8 M urea, 50 mM NaCl (to facilitate disruption of the strong inter-and intra-molecular interactions) and the protease inhibitor cocktail described in Example 3. Isoelectric focusing (IEF) was carried out using a Protean IEF cell (Bio-Rad) according to the manufacturer's protocol. Homogenized myofibrils (approximately 2 µg) were diluted in rehydration buffer (8 M urea, 2.5 M thiourea, 2% (w/v) CHAPS, 0.5% (v/v) ampholytes (either pH 4.5–5.5 or 7–10), 50 mM dithiothreitol (DTT) and 0.01% (w/v) bromophenol blue). Immobilized pH gradient (IPG) Ready Strips (large 17 vcm strips, pH 4.5–5.5 linear gradient, Pharmacia or small 7 cm strips, pH 7–10.0 linear gradient, Bio-Rad) were actively rehydrated at 50 V for 10 hours, then subjected to the following conditions using rapid-voltage ramp method: 100 V for 5 minutes, 500 V for 5 minutes, 1000 V for 5 minutes and 4000 V for 25 kVh (small strips) or 8000 V for 65 kVh (large strips) at 20° C. IPG strips were incubated for 15 minutes in equilibration buffer (50 mM Tris-HCl, pH 8.8, 6 M urea, 30% (v/v) glycerol, 2% (w/v) SDS) supplemented with 10 mg/ml DTT followed by an additional 15 minute incubation in equilibration buffer supplemented with 25 mg/ml iodoacetamide. Prepared IEF strips were embedded in a 5% acrylamide stacking gel and resolved by 12% SDS-PAGE using either a Protean II XL system (large strips) (Bio-Rad) or the Protean III system (small strips) (Bio-Rad). Electrophoresis was carried out at 50 V until the dye front was within 1 cm of the bottom of the gel.

Example 6

Silver Staining of Large (17 cm) 2-DE Gels

Gels were silver-stained according to the protocol of Shevchenko et al. (1996 Anal. Chem. 68:850–858) for compatibility with subsequent analysis of proteins by mass spectrometry. Gels were fixed for 1 hour in 50% v/v methanol, 5% (v/v) acetic acid followed by 10 minutes in 50% (v/v) methanol, then 2×10 minutes in deionized distilled water ($ddH_2O$). Gels were sensitized for 1 minute in 0.02% (w/v) sodium thiosulfate, followed by 2×1 minute $ddH_2O$ washes. Proteins were then visualized with developing solution (2% (w/v) sodium carbonate, 0.04% (v/v) formalin) and process was stopped with 5% (v/v) acetic acid.

Example 7

Protein Transfer and Western Blotting

Small 2-DE gels were equilibrated in 2×10 minute washes in 10 mM CAPS buffer (pH 11), then transferred in the same buffer to nitrocellulose at 100 V for 45 minutes. Nitrocellulose membranes were incubated in 1% (v/v) blocking solution (Roche Diagnostics) for 1 hour. Nitrocellulose membranes were subsequently washed 2×5 minutes with phosphate-buffered saline/Tween-20 (PBS-T) (137 mM NaCl, 2.7 mM KCl, 10.1 mM $Na_2HPO_4$, 1.8 mM $KH_2PO_4$ and 0.1% (v/v) Tween-20). Detection of fast skeletal troponin I was done using the antitroponin I monoclonal antibody clones FI-32, 3I-35, 8I-7 (Spectral Diagnostics), and polyclonal antibody clone sc-8120 (Santa Cruz Biotechnology, Inc.). Nitrocellulose membranes were incubated with the primary antibody (1 µg/ml) in PBS-T (137 mM NaCl, 2.7 mM KCl, 10.1 $Na_2HPO_4$, 1.8 mM $KH_2PO_4$ and 0.1% (v/v) Tween-20) with 1% (v/v) blocking solution for 1 hour followed by 3×5 minute washes with PBS-T. Proteins were detected using ImmunoStar chemiluminescent (Bio-Rad, exposing membrane to Kodak X-Omat blue XB-1 film (Perkin Elmer Life Sciences). Western blotting for desmin and troponin T were carried out as above using the mAbs DE-U-10 (Sigma) and JLT-12 (Sigma), respectively.

Example 8

Image Analysis of Silver Stained 2-DE gels

Gels were digitized at a resolution of 150 dpi using a PowerLook II scanner (UMAX Data Systems, Inc.) on a Sun Ultra computer (Sun Microsystems, Inc). Protein spots were located and matched to spots on other gels using Investigator HT Proteome Analyzer 1.0.1 software (Genomic Solutions, Inc.). Gels were normalized to compensate for differences in protein loading and level of silver staining. A computer-derived composite image was generated from four real gels to provide a virtual 2-DE for comparing the myofibril proteins from sham-EDL and I/R EDL.

Example 9

Image Analysis of Volume Charts of 2-DE Western Blots

In order to compare 2-DE western blots for fast skeletal troponin I, exposures were scanned (see Example 6) and 3-dimensional volume (density) charts were generated. Western blot exposures within 10% of the upper linear range were used for analysis.

Example 10

Dephosphorylation

Protein phosphatase-1 (1 μl; 10 U) (Sigma) was added to 10 μl reaction buffer (100 mM NaCl, 1 mM DTT, 10 mM MgCl2 and 50 mM Tris-HCl, pH 7.9) and 2 μg of homogenized myofibrils for 1 hour at 37° C. The reaction was terminated with the addition of 240 μl of IPG buffer. Samples were then analyzed by 2-DE as described in Example 6.

Example 11

In Vivo Model of Diaphragmatic Fatigue

Rats (n=11, Sprague Dawley, Charles River, Montreal, QC) weighing 300 to 460 g, were anesthetized with sodium pentobarbital (65 mg/kg i.p., supplemented as required with 0.8 to 1.6 mg, i.v., to prevent a pedal reflex). Atropine sulfate (0.05 mg/kg, s.c.) was administered to reduce tracheal secretions. Once a surgical plane of anesthesia was established, the rat was placed supine on a heating pad (Fine Science Tolls, North Vancouver, BC) and a thermal probe inserted into the rectum and secured to the tail; body temperature was maintained at approximately 37.5° C.

An incision was made in the midline of the neck and the skin retracted (Small Animal Retraction System, Fine Science Tolls, North Vancouver, BC). Both right and left sternohyoid muscles were isolated and excised. The right carotid artery (for measuring blood pressure and sampling arterial blood gases; Radiometer ABL-3, Copenhagen, Denmark) and jugular vein were cannulated and a tracheal cannula inserted. Tracheal pressure (Ptr; Gould Statham PM5E, Hato Rey, Puerto Rico) was recorded from one port of this cannula.

The left phrenic nerve was prepared as follows to ensure stable recordings over many hours. After isolating the nerve from surrounding tissues, a 3×25 mm piece of parafilm was positioned beneath it. Using a glass hook, the nerve was lifted over a small bipolar silver hook electrode (inter-electrode distance approximately 1.5 mm). Small pieces of hardened low melting point paraffin wax were positioned between the nerve and parafilm for additional isolation. To minimize movement of the nerve/electrode/wire assembly, the wires were sutured to the skin. Last, liquid low melting point wax was pipetted over the entire nerve/electrode assembly. A ground wire was then attached to a muscle in the neck. Phrenic nerve activity was amplified and filtered (100 to 10,000 Hz; Grass P-511, Quincy, Mass.) and integrated (Paynter filter, time constant 50 ms).

To record transdiaphragmatic pressure (Pdi), warm water (approximately 3 ml) was first injected into the stomach via an oral catheter. After placing rubber tubing over the lower incisors, the tip of a pressure transducer (Millar SPR 524, Houston, Tex.) was advanced into the stomach, as indicated by a positive deflection during inspiration or when slight pressure was applied to the upper abdomen. The tip of the second transducer was then placed in the esophagus where a maximal deflection free of cardiac artifacts was obtained. The difference between abdominal (Pab) and esophageal (Pes) pressures is the Pdi.

All signals (blood pressure, integrated phrenic activity (Phr), and tracheal pressure Ptr, Pes, Pab, and Pdi, were acquired (CED Spike2, Cambridge, UK) using a computer. Sampling frequency was 200/second for the integrated phrenic signal and 100/second for the others.

The loading protocol was performed as follows. A two-way valve (Hans Rudolf series 2300, Kansas City, Mo.) was attached to one port of the tracheal cannula; a section of latex tubing approximately 4 cm in length was attached to the inspiratory. After 15 minutes of breathing on circuit, a blood sample was taken. Before starting, control blood gases included $PaO_2 > 65$ mmHg since preliminary experiments indicated that rats with lower $PaO_2$s were unlikely to breathe successfully against an inspiratory resistive load (IRL). After this value was attained, the inspiratory line was occluded for 30 second. A Ptr of 50–60% of the peak Ptr obtained during occluded inspiratory efforts was used for the subsequent IRL, applied approximately 15 minutes after the occlusion.

IRL was accomplished by tightening a clamp on the inspiratory line. This was applied over approximately 15 minutes, as initial experiments indicated that too rapid an imposition of IRL often resulted in respiratory arrest.

What is claimed is:

1. An isolated post-translationally modified myofilament protein comprising a troponin I protein comprising SEQ ID NO:1, 2, 3, 4, 5, 6, 7, 8, 10, 11, 12 or 13 and phosphorylated at a site in the C terminal region or adjacent to its minimal inhibitory region.

2. The isolated posttranslationally modified myofilament protein of claim 1 comprising SEQ ID NO:5.

3. The isolated posttranslatiorially modified myofilament protein of claim 1 comprising SEQ ID NO:7.

4. The isolated posttranslatioflally modified myofilament protein of claim 1 comprising SEQ ID NO:10.

5. The isolated post-translationally modified myofilament protein of claim 1 wherein the troponin I is phosphorylated in the C terminal region and adjacent to its minimal inhibitory region.

6. The isolated post-translationally modified myofilament protein of claim 1 wherein the troponin I is fast skeletal troponin I comprising SEQ ID NO:1, 3, 4, 5 or 6 and phosphorylated at serine 117 or serine 168.

7. The isolated post-translationally modified myofilament protein of claim 1 wherein the troponin I is fast skeletal troponin I comprising SEQ ID NO:1, 3, 4, 5 or 6 and phosphorylated at serine 117 and serine 168.

8. The isolated post-translatioflally modified myofilament protein of claim 1 wherein the troponin I is human cardiac troponin I comprising SEQ ID NO:10 and phosphorylated at serine 149 or serine 198.

9. The isolated post-translationally modified myofilament protein of claim 1 wherein the troponin I is human cardiac troponin I comprising SEQ ID NO:10 and phosphorylated at serine 149 and serine 198.

10. The isolated post-translationally modified inyofilament protein of claim 1 wherein the troponin I is rat cardiac troponin I comprising SEQ IDNO:2 and phosphorylated at serine 150 or serine 199.

11. The isolated post-translationallY modified myofilarnent protein of claim 1 wherein the troponin I is rat cardiac troponiri I comprising SEQ ID NO:2 and phosphorylated at serine 150 and serine 199.

12. The isolated post-translationallY modified myofilament protein of claim 1 wherein the troponin I is slow, skeletal tropoflin I comprising SEQ ID NO:7 or 8 and phosphorylated at serine 118 or serine 168.

13. The isolated post-translationally modified myofilament protein of claim 1 wherein the troponin I is slow skeletal troponin I comprising SEQ ID NO:7 or 8 and phosphorylated at serine 118 and serine 168.

* * * * *

UNITED STATES PATENT AND TRADEMARK OFFICE
CERTIFICATE OF CORRECTION

PATENT NO. : 7,196,169 B2
APPLICATION NO. : 10/270838
DATED : March 27, 2007
INVENTOR(S) : Van Eyk et al.

It is certified that error appears in the above-identified patent and that said Letters Patent is hereby corrected as shown below:

Column 49, Line 34: Please delete "posttranslationally" and insert --post-translationally--.

Column 49, Line 36: Please delete "posttranslatiorally" and insert --post-translationally--.

Column 49, Line 38: Please delete "posttranslatioflally" and insert --post-translationally--.

Column 49, Line 52: Please delete "postr-translatioflally" and insert --post-translationally--.

Column 50, Line 28: Please delete "SEQ ID NO:10and" and insert --SEQ ID NO:10 and--.

Column 50, Line 32: Please delete "SEQ ID NO:10and" and insert --SEQ ID NO:10 and--.

Column 50, Lines 35-36: Please delete "inyofilament" and insert --myofilament--.

Column 50, Line 37: Please delete "SEQ IDNO:2" and insert -- SEQ ID NO:2--.

Column 50, Line 39: Please delete "post-translationallY" and insert --post-translationally--.

Column 50, Lines 39-40: Please delete "myofilarnent" and insert --myofilament--.

Column 50, Line 41: Please delete "troponiri" and insert --troponin--.

Column 50, Line 43: Please delete "post-translationallY" and insert --post-translationally--.

Column 50, Line 44: Please delete "slow," and insert --slow--.

UNITED STATES PATENT AND TRADEMARK OFFICE
CERTIFICATE OF CORRECTION

PATENT NO. : 7,196,169 B2
APPLICATION NO. : 10/270838
DATED : March 27, 2007
INVENTOR(S) : Van Eyk et al.

It is certified that error appears in the above-identified patent and that said Letters Patent is hereby corrected as shown below:

Column 50, Line 45: Please delete "tropoflin" and insert --troponin--.

Signed and Sealed this

Fourth Day of December, 2007

JON W. DUDAS
*Director of the United States Patent and Trademark Office*